(12) United States Patent
Kappel et al.

(10) Patent No.: US 10,316,077 B2
(45) Date of Patent: Jun. 11, 2019

(54) CELL-PENETRATING ATF5 POLYPEPTIDES AND USES THEREOF

(71) Applicant: Sapience Therapeutics, Inc., Harrison, NY (US)

(72) Inventors: Barry Jay Kappel, Pelham, NY (US); Jimmy Andrew Rotolo, Port Washington, NY (US); Gene Merutka, Phoenixville, PA (US)

(73) Assignee: Sapience Therapeutics, Inc., Harrison, NY (US)

( * ) Notice: Subject to any disclaimer, the term of this patent is extended or adjusted under 35 U.S.C. 154(b) by 0 days.

(21) Appl. No.: 15/898,536

(22) Filed: Feb. 17, 2018

(65) Prior Publication Data
US 2018/0237499 A1    Aug. 23, 2018

Related U.S. Application Data

(60) Provisional application No. 62/460,975, filed on Feb. 20, 2017.

(51) Int. Cl.
| | | |
|---|---|---|
| *A61K 38/58* | (2006.01) | |
| *C07K 14/82* | (2006.01) | |
| *C07K 14/47* | (2006.01) | |
| *A61P 35/00* | (2006.01) | |
| *A61K 38/00* | (2006.01) | |

(52) U.S. Cl.
CPC .............. *C07K 14/82* (2013.01); *A61P 35/00* (2018.01); *C07K 14/4705* (2013.01); *A61K 38/00* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 5,942,433 A | 8/1999 | Vinson et al. | |
| 5,955,593 A | 9/1999 | Korsmeyer | |
| 5,998,583 A | 12/1999 | Korsmeyer | |
| 6,221,355 B1 | 4/2001 | Dowdy | |
| 6,303,576 B1 | 10/2001 | Blaschuk et al. | |
| 6,361,968 B1 | 3/2002 | Vinson et al. | |
| 6,468,754 B1 | 10/2002 | Greene et al. | |
| 6,485,977 B1 | 11/2002 | Collmer et al. | |
| 7,888,326 B2 | 2/2011 | Greene et al. | |
| 8,158,420 B2 | 4/2012 | Greene et al. | |
| 9,758,555 B1 | 9/2017 | Greene et al. | |
| 9,758,556 B1 | 9/2017 | Greene et al. | |
| 10,155,796 B2 | 12/2018 | Greene et al. | |
| 2002/0160002 A1 | 10/2002 | Gelman | |
| 2007/0092495 A1 | 4/2007 | Greene et al. | |
| 2012/0093919 A1 | 4/2012 | Bertino et al. | |
| 2012/0238462 A1 | 9/2012 | Greene et al. | |
| 2016/0008480 A1 | 1/2016 | Lee et al. | |
| 2016/0046686 A1* | 2/2016 | Greene | A61K 38/1709 514/19.3 |
| 2018/0002389 A1 | 1/2018 | Greene et al. | |

FOREIGN PATENT DOCUMENTS

| | | |
|---|---|---|
| WO | WO 2008/072777 | 6/2008 |
| WO | WO 2008/151037 | 12/2008 |
| WO | WO 2011/097513 | 8/2011 |
| WO | WO 2013/013105 | 1/2013 |

OTHER PUBLICATIONS

Olive, Michelle et al, "Design of a c/ebp-specific, dominant-negative bzip protein with both inhibitory and gain of function properties." J. Biol. Chem. (1996) 271(4) p. 2040-2047.*
Acharya et al., Experimental identification of homodimerizing B-ZIP families in *Homo sapiens*, J. Struct. Biol. 155:130-139, 2006.
Angelastro et al., Regulated Expression of ATF5 Is Required for the Progression of Neural Progenitor Cells to Neurons, J. Neurosci. 23:4590-4600, 2003.
Angelastro et al., Downregulation of ATF 5 Is Required for Differentiation of Neural Progenitor Cells into Astrocytes, J. Neurosci, 25:3889-3899, 2005.
Angelastro et al., Selective destruction of glioblastoma cells by interference with the activity or expression of ATF5, Oncogene 25:907-916, 2006.
Araghi et al., Designing helical peptide inhibitors of protein-protein interactions, Curr. Opin. Struct. Biol. 39:27-38, 2016.
Arias et al,, Regulated ATF5 loss-of-function in adult mice blocks formation and causes regression/eradication of gliomas, Oncogene 31:739-751, 2012.
Cates et al., Regression/Eradication of gliomas in mice by a systematicallly-deliverable ATF5 dominant-negative peptide, Oncotarget 11:12718-12730, 2016.
Ciaccio et al., High-yield expression in *E. coli* and refolding of the bZIP domain of activating transcription factor 5, Protein Expr. Purif. 62:235-243, 2008.

(Continued)

*Primary Examiner* — Fred H Reynolds
(74) *Attorney, Agent, or Firm* — Grimes & Yvon LLP

(57) ABSTRACT

Provided are cell-penetrating ATF5 polypeptides having a cell-penetrating region and an ATF5 leucine zipper region, compositions comprising the ATF5 polypeptides, and methods of treating a tumor and promoting cytotoxicity in a neoplastic cell using the ATF5 polypeptides.

20 Claims, 8 Drawing Sheets

Specification includes a Sequence Listing.

(56) References Cited

OTHER PUBLICATIONS

Ciaccio et al., Influence of the Valine Zipper Region on the Structure and Aggregation of the Basic Leucine Zipper (bZIP) Domain of ATF5, Mol. Pharm. 9:3190-3199, 2012.
Dluzen et al., BCL-2 Is a Downstream Target of ATF5 That Mediates the Prosurvival Function of ATF5 in a Cell Type-dependent Manner, J. Biol. Chem. 286:7705-7713, 2011.
Greene et al., The transcription factor ATF5: role in neurodevelopment and neural tumors, J. Neurochem. 108:11-22, 2009.
Heitz et al., Twenty years of cell-penetrating peptides: from molecular mechanisms to therapeutics, Brit. J. Pharm. 157:195-206, 2009.
Herve et al., CNS Delivery via Adsorptive Transcytosis, AAPS J. 10:455-472, 2008.
Karpel-Massler et al., A Synthetic Cell-Penetrating Dominant-Negative ATF5 Peptide Exerts Anticancer Activity . . . , Clin. Cancer Res. doi: 10.1158/1078-0432.CCR-15-2827, 2016.
Krautwald et al., Inhibition of regulated cell death by cell-penetrating peptides, Cell. Mol. Life Sci. 73:2269-2284, 2016.
Krylov et al., Extending dimerization interfaces: the bZIP basic region can form a colied coil, EMBO J. 14:5329-5337, 1995.
Krylov et al., A general method to design dominant negatives to B-HLHZip proteins that abolish DNA binding, Proc. Natl. Acad. Sci., USA 94:12274-12279, 1997.
Lee et al., Reciprocal Actions of ATF5 and Shh in Proliferation of Cerebellar Granule Neuron Progenitor Cells, Dev. Neurobiol. 72:789-804, 2012.
Li, et al., Identification of a Novel DNA Binding Site and a Transcriptional Target for ATF5 in C6 Glioma and MCF-7 Breast Cancer Cells, Mol. Cancer Res. 7:933-943, 2009.
Liu et al., Nucleophosmin (NPM1/B23) Interacts with Activating Transcription Factor 5 (ATF5) Protein . . . , J. Biol. Chem. 287:19599-19609, 2012.
Mason et al., ATF5 regulates the proliferation and differentiation of oligodendrocytes, Mol. Cell. Neurosci. 29:372-380, 2005.
Moll et al., Attractive Interhelical Electrostatic Interactions in the Proline- and Acidic-Rich Region (PAR) Leucine Zipper Subfamily . . . , J. Biol. Chem. 275:34826-34832, 2000.
Monaco et al., The transcription factor ATF5 is widely expressed in carcinomas, and interference with its function selectively kills . . . , Int. J. Cancer 120:1883-1890, 2007.
Munyendo et al., Cell Penetrating Peptides in the Delivery of Biophharmaceuticals, Biomolecules 2:187-202, 2012.
Olive et al., A Dominant Negative to Activation Protein-1 (AP1) That Abolishes DNA Binding and Inhibits Oncogenesis, J. Biol. Chem. 272:18586-18594, 1997.
Schmidt et al., Identification of Short Hydrophobic Cell-Penetrating Peptides for Cytosolic Peptide Delivery by Rational Design, Bioconjugate Chem. 28:382-389, 2017.
Sears et al., The transcription factor ATF5: role in cellular differentiatio, stress responses, and cancer, Oncotarget 8:84595-84609, 2017.
UniProtKB—Q9Y2D1 (ATF5_Human), 2010.
Vinson et al., Dimerization specificity of the leucine zipper-containing bZIP motif on DNA binding: prediction and rational design, Genes & Devel. 7:1047-1058, 1993.
Zou et al., Cell-Penetrating Peptide-Mediating Therapeutic Molecule Delivery into the Central Nervous System, Curr. Neuropharmacol, 11:197-208, 2013.

* cited by examiner

Figure 1A

LEQRAEELARENEELLEKEAEELEQENAELEGECQGLEARNRELRERAESVEREI
QYVKDLLIEVYKARSQRTRSA (SEQ ID NO: 1)

Figure 1B

*RQIKIWFQNRRMKWKK*LEQRAEELARENEELLEKEAEELEQENAELEGECQGLEAR
NRELRERAESV (SEQ ID NO: 2)

Figure 1C

*RQIKIWFQNRRMKWKK*LEGECQGLEARNRELKERAESV (SEQ ID NO: 3)

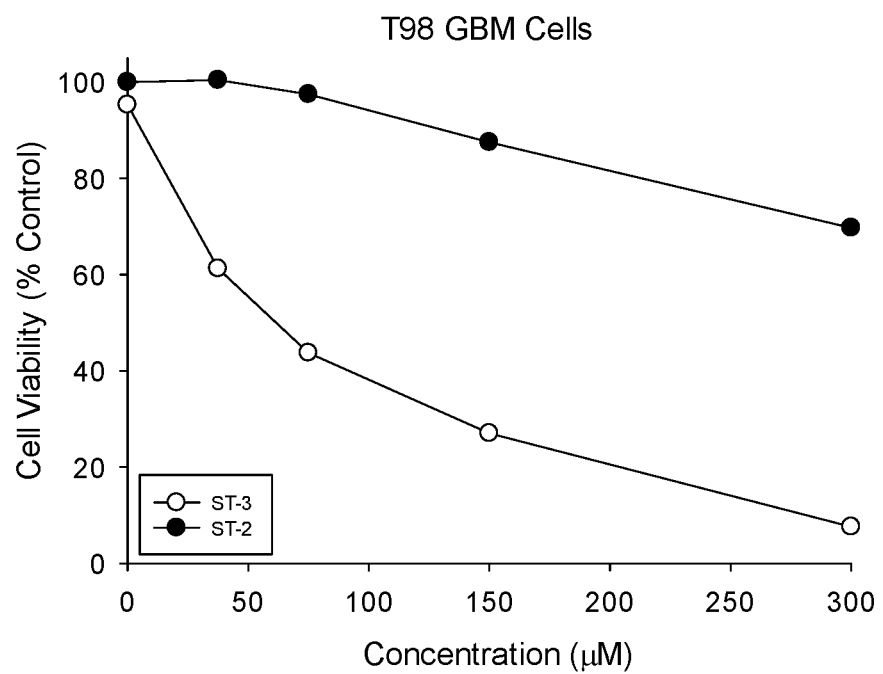

CELL-PENETRATING ATF5 POLYPEPTIDES AND USES THEREOF

CROSS-REFERENCE TO RELATED APPLICATIONS

This application claims the benefit of priority of U.S. Provisional Patent Application No. 62/460,975, filed on Feb. 20, 2017, the entire contents of which are incorporated by reference.

BACKGROUND

Activating transcription factor 5 (ATF5) is a member of the ATF/CREB (cAMP response element binding protein) family of basic leucine zipper proteins. In the normal developing brain, ATF5 is highly expressed in neural progenitor/neural stem cells where it blocks cell cycle exit and promotes cell proliferation, thereby inhibiting neurogenesis and gliogenesis. ATF5 downregulation is required to permit neuroprogenitor cell cycle exit and differentiation into either neurons, astrocytes, or oligodendroglia (Greene et al. 2009; Sheng et al. 2010a; Sheng et al. 2010b; Arias et al. 2012).

In addition to its role in normal development of the nervous system, ATF5 has also emerged as an oncogenic factor that promotes survival of gliomas and other tumors. A number of studies have demonstrated that ATF5 is highly expressed in a variety of cancers, including glioblastoma, breast, pancreatic, lung, and colon cancers, and is essential for glioma cell survival (Monaco et al. 2007; Sheng et al. 2010a). In the context of gliomas, overexpression of ATF5 inversely correlates with disease prognosis and survival, i.e., glioma patients with higher ATF5 expression have significantly worse outcomes than patients with lower ATF5 expression.

In cancer cells, genes that induce apoptosis are often inactivated or down-regulated, whereas anti-apoptotic genes are frequently activated or overexpressed. Consistent with this paradigm, ATF5 upregulates transcription of anti-apoptotic proteins, including B-cell leukemia 2 (Bcl-2) and myeloid cell leukemia 1 (Mcl-1), promoting tumor cell survival (Sheng et al., 2010b; Chen et al., 2012).

Based on its role in antagonizing apoptosis and promoting cell survival, combined with high expression levels in cancer cells but not in most normal tissues, ATF5 has been identified as an attractive potential therapeutic target for cancer therapy. For instance, interference with ATF5 activity or expression promotes induction of apoptosis in glioblastoma cells in vitro and in vivo without affecting normal astrocytes (Karpel-Massler et al. 2016).

In terms of structure, ATF5 is a 282-amino acid eukaryotic transcription factor with an N-terminal acidic activation domain and a C-terminal basic leucine zipper (bZIP) domain. The bZIP domain contains a DNA-binding region and a leucine zipper region. The leucine zipper is a common structural motif, having a leucine at every seventh amino acid in the dimerization domain. bZIP transcription factors homo- and/or hetero-dimerize via their leucine zippers to specifically bind to DNA. Wild-type human, rat, and murine ATF5 have the amino acid sequences set forth in NCBI Accession No. NP_001180575, NP_758839, and NP_109618, respectively.

NTAzip-ATF5 (FIG. 1A) is an ATF5 inhibitor in which the ATF5 N-terminal activation domain is deleted and the DNA binding domain is replaced with an engineered enhanced leucine zipper, i.e., an amphipathic acidic α-helical sequence containing heptad repeats with a leucine at every seventh residue, which extends the wild-type ATF5 leucine zipper region (Angelastro et al. 2003). Cell-penetrating dominant negative ATF5 (CP-d/n-ATF5) molecules are improved versions of NTAzip-ATF5, which contain a cell-penetrating domain and a truncated ATF5 leucine zipper (relative to wild-type), along with an extended leucine zipper sequence (US 2016/0046686). One example of a CP-d/n ATF5 molecule, ST-2, is shown in 1B.

The present inventors have surprisingly discovered that ST-3 (FIG. 1C), a variant of a CP-d/n-ATF5 molecule that lacks the leucine zipper extension, induces cell death in neoplastic cells. Previous studies have demonstrated that the enhanced leucine zipper region is required for stability and inhibitory activity of dominant-negative bZIP inhibitors (Krylov et al. 1995; Olive et al. 1997; Moll et al. 2000; Acharya et al. 2006). Therefore, the discovery that the ATF5 polypeptides of the present invention retain their ability to specifically target and kill neoplastic cells in the absence of an extended leucine zipper region was unexpected.

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

Accordingly, the disclosure provides cell-penetrating polypeptide derivatives of wild-type ATF5 comprising a cell penetrating domain and an ATF leucine zipper domain, wherein an engineered enhanced leucine zipper sequence is absent, compositions and kits comprising the ATF5 polypeptides, and methods for treating cancer and inducing cytotoxicity in a neoplastic cell using the ATF polypeptides.

In one aspect, the invention provides a cell-penetrating ATF5 polypeptide consisting essentially of a cell-penetrating region and a truncated ATF5 leucine zipper region. In some embodiments, the truncated ATF5 leucine zipper region has an amino acid sequence selected from the group consisting of LEGECQGLEARNRELKERAESV (SEQ ID NO: 7) and LEGECQGLEARNRELRERAESV (SEQ ID NO: 8). In some embodiments, the polypeptide comprises a lactam bridge between positions of SEQ ID NO: 7 or SEQ ID NO: 8 selected from the group consisting of: E9 and RΔK13; AΔK10 and E14; and E17 and SΔK21.

In some embodiments, the cell-penetrating region has an amino acid sequence selected from the group consisting of: RQIKIWFQNRRMKWKK (SEQ ID NO: 20), RQLKLWFQNRRMKWKK (SEQ ID NO: 21), YGRKKRRQRRR (SEQ ID NO: 35), and YGRKKRRQRR (SEQ ID NO: 36).

In a further aspect, the invention provides a cell-penetrating ATF5 polypeptide comprising an amino acid sequence selected from the group consisting of:

```
                                           (SEQ ID NO: 3)
RQIKIWFQNRRMKWKKLEGECQGLEARNRELKERAESV;

(SEQ ID NO: 4)
RQIKIWFQNRRMKWKKLEGECQGLEARNRELRERAESV;
```

-continued

YGRKKRRQRRRLEGECQGLEARNRELKERAESV; (SEQ ID NO: 5)
and

YGRKKRRQRRRLEGECQGLEARNRELRERAESV. (SEQ ID NO: 6)

In one embodiment, the cell-penetrating ATF5 polypeptide comprises the amino acid sequence RQIKIWFQN-RRMKWKKLEGECQGLEARNRELKERAESV (SEQ ID NO: 3). In particular embodiments, the polypeptide comprises a lactam bridge between positions selected from the group consisting of: K13 and E20; E25 and RΔK29; AΔK26 and E30; and E33 and SΔK37.

In some embodiments, the cell-penetrating ATF5 polypeptide of the invention comprises an N-terminal acetyl group and/or a C-terminal amide group.

In some embodiments, the cell-penetrating ATF5 polypeptide of the invention is capable of crossing the blood-brain barrier (BBB).

Also provided is a composition comprising a cell-penetrating ATF5 polypeptide of the invention. In some embodiments, the composition is a pharmaceutical composition. Further provided is a kit comprising a cell-penetrating ATF5 polypeptide of the invention, and a nucleic acid molecule encoding a cell-penetrating ATF5 polypeptide of the invention.

The invention also provides an in vitro or ex vivo method of promoting cytotoxicity in a neoplastic cell, the method comprising contacting the neoplastic cell with a cell-penetrating ATF5 polypeptide of the invention.

The invention further provides an in vitro or ex vivo method of promoting cytotoxicity in a neoplastic cell, the method comprising introducing into the neoplastic cell an ATF5 polypeptide consisting essentially of an amino acid sequence selected from the group consisting of LEGECQGLEARNRELKERAESV (SEQ ID NO: 7) and LEGECQGLEARNRELRERAESV (SEQ ID NO: 8), or a nucleic acid molecule encoding an ATF5 polypeptide consisting essentially of an amino acid sequence selected from the group consisting of LEGECQGLEARNRELKERAESV (SEQ ID NO: 7) and LEGECQGLEARNRELRERAESV (SEQ ID NO: 8).

BRIEF DESCRIPTION OF THE DRAWINGS

FIG. 1A-1C show amino acid sequences of the ATF-5 polypeptides NTAzip-ATF5 (SEQ ID NO: 1) (FIG. 1A), ST-2 (SEQ ID NO: 2) (FIG. 1B), and ST-3 (SEQ ID NO: 3) (FIG. 1C). Where present, the extended leucine zipper domain is underlined, the Penetratin-1 cell penetrating domain is italicized, and the ATF-5 leucine zipper domain is bolded.

FIG. 3A-3C show that ST-3 causes cell death in vitro. ST-3 is more potent than ST-2 in HL60 promyelocytic leukemia (PML) cells (FIG. 3A) and in U251 GBM cells (FIG. 3B). In T98G glioblastoma cells, viability decreases upon exposure to ST-3 (FIG. 3C). Viability was assessed after 72 hours of drug exposure.

FIG. 6A shows that ST-3 represses tumor growth in a U87 subcutaneous tumor model. FIG. 6B shows that ST-3 delays tumor growth in a patient-derived mesenchymal GBM tumor xenograft model. FIG. 6C shows mean tumor volume in an HL-60 subcutaneous tumor model. Nu/Nu mice (n=4) were administered twice daily subcutaneous injections of ST-3 (25 mg/kg per dose).

DETAILED DESCRIPTION OF THE INVENTION

Figure 2:
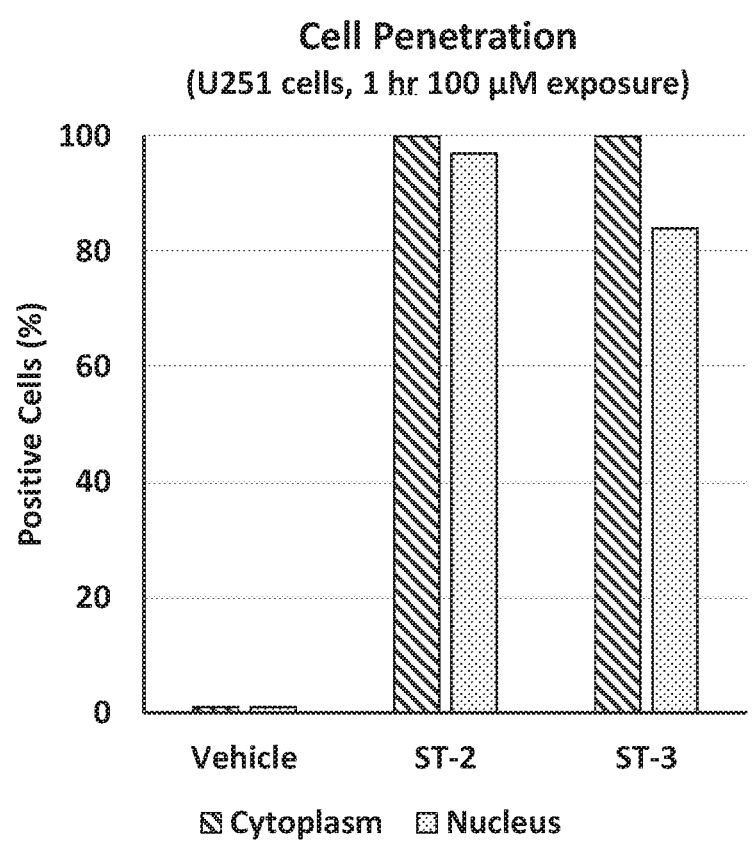
FIG. 2 shows that ST-3 rapidly enters U251 glioblastoma multiforme (GBM) cells and enters the nucleus. Cells were treated with 100 µM ST-2 or ST-3 for 1 hour prior to immunofluorescence staining and analysis by scanning cytometry.

The compounds and compositions described herein can be used to treat various conditions and diseases described herein. The compounds and compositions also have superior, unexpected properties including, but not limited to, in vitro and in vivo ability to be cytotoxic to neoplastic cells.

The practice of the present invention will employ, unless otherwise indicated, conventional techniques of pharmaceutics, formulation science, protein chemistry, cell biology, cell culture, molecular biology, transgenic biology, microbiology, recombinant DNA, and immunology, which are within the skill of the art.

In order that the present invention can be more readily understood, certain terms are first defined. Additional definitions are set forth throughout the disclosure. Unless defined otherwise, all technical and scientific terms used herein have the same meaning as commonly understood by one of ordinary skill in the art to which this invention is related.

Any headings provided herein are not limitations of the various aspects or embodiments of the invention, which can be had by reference to the specification as a whole. Accordingly, the terms defined immediately below are more fully defined by reference to the specification in its entirety.

All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

I. Definitions

The phraseology or terminology in this disclosure is for the purpose of description and not of limitation, such that the terminology or phraseology of the present specification is to be interpreted by the skilled artisan in light of the teachings and guidance.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Wherever embodiments are described with the language "comprising," otherwise analogous embodiments described in terms of "consisting of" and/or "consisting essentially of" are included.

Units, prefixes, and symbols are denoted in their Système International de Unites (SI) accepted form. Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

Amino acids are referred to herein by their commonly known three-letter symbols or by the one-letter symbols recommended by the IUPAC-IUB Biochemical Nomenclature Commission. Unless otherwise indicated, amino acid sequences are written left to right in amino to carboxy orientation.

The terms "polypeptide," "peptide," and "protein" are used interchangeably herein to refer to polymers of amino acids of any length and their salts. The polymer can be linear or branched, it can comprise modified amino acids, and can be interrupted non-amino acids. The terms also encompass an amino acid polymer that has been modified naturally or by intervention; for example, disulfide bond formation, lactam bridge formation, glycosylation, lipidation, acetylation, acylation, amidation, phosphorylation, or other manipulation or modification, such as conjugation with a labeling component or addition of a protecting group. Also included within the definition are, for example, polypeptides containing one or more analogs of an amino acid (including, for example, unnatural amino acids, etc.), as well as other modifications known in the art. In certain embodiments, the polypeptides can occur as single chains, covalent dimers, or non-covalent associated chains. Polypeptides can also contain one or more bridges or cross-links within the sequence. The spacing of cross-links between amino acids can be, for example, 3, 4, or 7 residues apart, preferably 3 or 4 residues apart. In some cases, the internal cross-link replaces the side chains of cross-linked residues. In some cases, the amino acid side chains are replaced with hydrocarbon chains. In some cases, the original amino acid(s) in the sequence are substituted with other amino acids so that a link can be made, for example, by bridging free amino and free carboxyl sidechain groups via a lactam. Substitution is denoted herein by a Δ between the original amino acid and the substituted amino acid. Formation of the cyclic compounds can be achieved by treatment with a dehydrating agent, with suitable protection if needed. The open chain (linear form) to cyclic form reaction can involve intramolecular-cyclization.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids, and aromatic amino acids. For further information concerning phenotypically silent substitutions in peptides and proteins, see, for example, Bowie et. al., Science 247:1306-1310 (1990). Table I below, conservative substitutions of amino acids are grouped by physicochemical properties; I: neutral and/or hydrophilic, II: acids and amides, III: basic, IV: hydrophobic, V: aromatic, bulky amino acids.

TABLE I

| I | II | III | IV | V |
|---|----|-----|----|----|
| A | N  | H   | M  | F  |
| S | D  | R   | L  | Y  |
| T | E  | K   | I  | W  |
| P | Q  |     | V  |    |
| G |    |     | C  |    |

In the Table II below, conservative substitutions of amino acids are grouped by physicochemical properties; VI: neutral or hydrophobic, VII: acidic, VIII: basic, IX: polar, X: aromatic.

TABLE II

| VI | VII | VIII | IX | X |
|----|-----|------|----|---|
| A  | D   | H    | M  | F |
| L  | E   | R    | S  | Y |
| I  |     | K    | T  | W |
| V  |     |      | N  | H |
| P  |     |      | Q  |   |
| G  |     |      | C  |   |

Methods of identifying conservative nucleotide and amino acid substitutions which do not affect protein function are well-known in the art (see, e.g., Brummell et al., *Biochem.* 32:1180-1187 (1993); Kobayashi et al., *Protein Eng.* 12(10):879-884 (1999); and Burks et al., *Proc. Natl. Acad. Sci. U.S.A.* 94:412-417 (1997)).

The terms "identical" or percent "identity" in the context of two or more nucleic acids or polypeptides, refers to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms, or by visual inspection. Various algorithms and software are known in the art that can be used to obtain alignments of amino acid or nucleotide sequences.

One such non-limiting example of a sequence alignment algorithm is described in Karlin et al., *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)), can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS* 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used. Other resources for calculating identity include methods described in *Computational Molecular Biology* (Lesk ed., 1988); *Biocomputing: Informatics and Genome Projects* (Smith ed., 1993); *Computer Analysis of Sequence Data, Part* 1 (Griffin and Griffin eds., 1994); *Sequence Analysis in Molecular Biology* (G. von Heinje, 1987); *Sequence Analysis Primer* (Gribskov et al. eds., 1991); and Carillo et al., *SIAM J. Applied Math.*, 48:1073 (1988).

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

A "polynucleotide," as used herein can include one or more "nucleic acids," "nucleic acid molecules," or "nucleic acid sequences," and refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

An "isolated" molecule is one that is in a form not found in nature, including those which have been purified.

A "label" is a detectable compound that can be conjugated directly or indirectly to a molecule, so as to generate a "labeled" molecule. The label can be detectable on its own (e.g., radioisotope labels or fluorescent labels) or can catalyze chemical alteration of a substrate compound or composition that is detectable (e.g., an enzymatic label).

The term "operably linked" refers to the positioning of two or more molecules or sequences in a relationship permitting them to function in their intended manner. For example, a control sequence operably linked to a coding sequence is positioned in such a way that expression of the coding sequence is achieved under conditions compatible with the control sequence. Operable linkage can be covalent or non-covalent, depending upon the identity and intended function of the operably linked components.

"Binding affinity" generally refers to the strength of the sum total of non-covalent interactions between a single binding site of a molecule and its binding partner (e.g., a receptor and its ligand, an antibody and its antigen, two monomers that form a dimer, etc.). Unless indicated otherwise, as used herein, "binding affinity" refers to intrinsic binding affinity which reflects a 1:1 interaction between members of a binding pair. The affinity of a molecule X for its partner Y can generally be represented by the dissociation constant ($K_D$). Affinity can be measured by common methods known in the art, including those described herein. Low-affinity binding partners generally bind slowly and tend to dissociate readily, whereas high-affinity binding partners generally bind faster and tend to remain bound longer.

The affinity or avidity of a molecule for its binding partner can be determined experimentally using any suitable method known in the art, e.g., flow cytometry, enzyme-linked immunosorbent assay (ELISA), or radioimmunoassay (MA), or kinetics (e.g., KINEXA® or BIACORE™ or OCTET® analysis). Direct binding assays as well as competitive binding assay formats can be readily employed. (See, e.g., Berzofsky et al., "Antibody-Antigen Interactions," In *Fundamental Immunology*, Paul, W. E., ed., Raven Press: New York, N.Y. (1984); Kuby, Immunology, W. H. Freeman and Company: New York, N.Y. (1992)). The measured affinity of a particular binding pair interaction can vary if measured under different conditions (e.g., salt concentration, pH, temperature). Thus, measurements of affinity and other binding parameters (e.g., $K_D$ or Kd, $K_{on}$, $K_{off}$) are made with standardized solutions of binding partners and a standardized buffer, as known in the art.

An "active agent" is an ingredient that is intended to furnish pharmacological activity or other direct effect in the diagnosis, cure, mitigation, treatment, or prevention of disease, or to affect the structure or any function of the human body. The active agent can be in association with one or more other ingredients, and can be, but is not necessarily, in a finished dosage form. The terms "active agent" and "drug substance" are used interchangeably herein.

An "effective amount" of an active agent is an amount sufficient to carry out a specifically stated purpose.

The term "pharmaceutical composition" refers to a preparation that is in such form as to permit the biological activity of the active ingredient to be effective and which contains no additional components that are unacceptably toxic to a subject to which the composition would be administered. Such composition can be sterile and can comprise a pharmaceutically acceptable carrier, such as physiological saline. Suitable pharmaceutical compositions can comprise one or more of a buffer (e.g. acetate, phosphate or citrate buffer), a surfactant (e.g. polysorbate), a stabilizing agent (e.g. polyol or amino acid), a preservative (e.g. sodium benzoate), a penetration enhancer, an absorption promoter to enhance bioavailability and/or other conventional solubilizing or dispersing agents. Choice of excipients depends upon dosage form, the active agent to be delivered, and the disease or disorder to be treated or prevented.

A "subject" or "individual" or "animal" or "patient" or "mammal," is any subject, particularly a mammalian subject, for whom diagnosis, prognosis, or therapy is desired. Mammalian subjects include humans, domestic animals, farm animals, sports animals, and laboratory animals including, e.g., humans, non-human primates, canines, felines, porcines, bovines, equines, rodents, including rats and mice, rabbits, etc.

Terms such as "treating" or "treatment" or "to treat" or "alleviating" or "to alleviate" refer to therapeutic measures that cure, slow down, lessen symptoms of, and/or halt progression of an undesired physiological condition, a diagnosed pathologic condition, disease, or disorder. Thus, those in need of treatment include those already with the disorder. In certain embodiments, a subject is successfully "treated" for a disease or disorder if the patient shows, e.g., total, partial, or transient alleviation or elimination of symptoms associated with the condition, disease, or disorder; diminishment of the extent of the condition, disease, or disorder; stabilization (i.e., not worsening) of the condition, disease, or disorder; delay in onset or slowing of progression of the condition, disease or disorder; amelioration of the condition, disease, or disorder, including partial or total remission; and/or prolonging survival, as compared to expected survival if not receiving treatment. In the context of the present invention, reduction of tumor volume is one example of treatment. Tumor volume can be monitored by any known method, including magnetic resonance imaging, computed tomographic imaging, positron emission tomography, sonography, mammography, and physical measurement.

"Prevent" or "prevention" refer to prophylactic or preventative measures that prevent and/or slow the development of a targeted pathologic condition or disorder. Thus, those in need of prevention include those prone to have or susceptible to the disorder. In certain embodiments, a disease or disorder is successfully prevented if the patient develops, transiently or permanently, e.g., fewer or less severe symptoms associated with the disease or disorder, or a later onset of symptoms associated with the disease or disorder, than a patient who has not been subject to the methods of the invention.

The terms "inhibit," "block," and "suppress" are used interchangeably and refer to any statistically significant decrease in occurrence or activity, including full blocking of the occurrence or activity. For example, "inhibition" can refer to a decrease of about 10%, 20%, 30%, 40%, 50%, 60%, 70%, 80%, 90% or 100% in activity or occurrence. An "inhibitor" is a molecule, factor, or substance that produces a statistically significant decrease in the occurrence or activity of a process, pathway, or molecule.

In functional assays, "$EC_{50}$" is the concentration that reduces a biological response by 50% of its maximum. In the case of ATF5 polypeptides, $EC_{50}$ is measured as the concentration that reduces cell viability by 50% of its maximum. $EC_{50}$ can be calculated by any number of means known in the art.

A "neoplastic cell" or "neoplasm" typically has undergone some form of mutation/transformation, resulting in abnormal growth as compared to normal cells or tissue of the same type. Neoplasms include morphological irregularities, as well as pathologic proliferation. Neoplastic cells can be benign or malignant. Malignant neoplasms, i.e., cancers, are distinguished from benign in that they demonstrate loss of differentiation and orientation of cells, and have the properties of invasion and metastasis.

A "solid tumor" is a mass of neoplastic cells. A "liquid tumor" or a "hematological malignancy" is a blood cancer of myeloid or lymphoid lineage. Hematological malignancies include leukemias, lymphomas, and myelomas. Examples of leukemia include acute lymphoblastic leukemia (ALL), acute myelogenous leukemia (AML), chronic lymphocytic leukemia (CLL), chronic myelogenous leukemia (CML), and acute monocytic leukemia (AMoL). Examples of lymphoma include Hodgkin's lymphoma and non-Hodgkin's lymphoma. Multiple myeloma is an example of a myeloma.

II. ATF5 Polypeptides and Compositions

Cell-Penetrating Peptides

The ATF5 polypeptides of the present invention preferably comprise a cell-penetrating domain or cell-penetrating peptide (CPP). The terms "cell-penetrating domain," "cell-penetrating region," and "cell-penetrating peptide" are used interchangeably herein.

CPPs are short (typically about 6-40 amino acids) peptides that are able to cross cell membranes. Peptides referred to as nuclear localization sequences are a subset of CPPs. Many CPPs are capable of crossing the blood-brain barrier (BBB). In some embodiments, the CPP is 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 amino acids in length, including ranges having any of those lengths as endpoints, for example, 10-30 amino acids. CPPs are typically water soluble, cationic or amphipathic, and rich in basic amino acids (e.g., lysine and/or arginine residues). CPPs can also be positively charged amphipathic peptides, or peptides that are hydrophobic, containing only apolar residues with low net charge or hydrophobic amino acid groups. CPPs have the ability to transport covalently or non-covalently linked molecular cargo, such as polypeptides, polynucleotides, and nanoparticles, across cell membranes and the BBB. The translocation can be endocytotic or energy-independent (i.e., non-endocytotic) via translocation. Numerous CPPs are described and characterized in the literature (see, e.g., Handbook of Cell-Penetrating Peptides (2d ed. Ulo Langel ed., 2007); Hervé et al. 2008; Heitz et al. 2009; Munyendo et al. 2012; Zou et al. 2013; Krautwald et al. 2016). A curated database of CPPs is maintained at crdd.osdd.net/raghava/cppsite (Gautam et al. 2012).

Non-limiting examples of CPPs suitable for use in the present invention include peptides derived from proteins, such as from *Drosophila* antennapedia transcription factor (Penetratin and its derivatives RL-16 and EB1) (Derossi et al. 1998; Thorén et al. 2000; Lundberg et al. 2007; Alves et al. 2008); from HIV-1 trans-activator of transcription (Tat) (Vivès et al. 1997; Hällbrink et al. 2001); from rabies virus glycoprotein (RVG) (Kumar et al. 2007); from herpes simplex virus VP22 (Elliott et al. 1997); from antimicrobial protegrin 1 (SynB) (Rousselle et al. 2001), from rat insulin 1 gene enhancer protein (pIS1) (Kilk et al. 2001; Magzoub et al. 2001); from murine vascular endothelial cadherin (pVEC) (Elmquist et al. 2001); from human calcitonin (hCT) (Schmidt et al. 1998); and from fibroblast growth factor 4 (FGF4) (Jo et al. 2005). CPPs suitable for use in the invention also include synthetic and chimeric peptides, such as Transportan (TP) and its derivatives (Pooga et al. 1998; Soomets et al. 2000); membrane translocating sequences (MTSs) (Brodsky et al. 1998; Lindgren et al. 2000; Zhao et al. 2001), such as the MPS peptide (also known as fusion sequence-based peptide or FBP) (Chaloin et al. 1998); sequence signal-based peptide (SBP) (Chaloin et al. 1997); model amphipathic peptide (MAP) (Oehlke et al. 1998; Scheller et al. 1999; Hällbrink et al. 2001), translocating peptide 2 (TP2) (Cruz et al. 2013), MPG (Morris et al. 1997; Kwon et al. 2009), Pep-1 (Morris et al. 2001; Muñoz-Morris et al. 2007), and poly-arginine (e.g., $R_7$-$R_{12}$) (Mitchell et al. 2000; Wender et al. 2000; Futaki et al. 2001; Suzuki et al. 2002). Representative but non-limiting CPP sequences are shown in Table 1.

TABLE 1

| Peptide | Sequence |
| --- | --- |
| *C. elegans* SDC3 | FKKFRKF (SEQ ID NO: 9) |
| CADY-K | GLWRALWRLLRSLWRLLWK (SEQ ID NO: 10) |
| EB1 CPP | LIRLWSHLIHIWFQNRRLKWKKK (SEQ ID NO: 11) |

TABLE 1-continued

| Peptide | Sequence |
|---|---|
| FBP CPP | GALFLGWLGAAGSTMGAWSQPKKKRKV (SEQ ID NO: 12) |
| FGF4 CPP | AAVALLPAVLLALLAP (SEQ ID NO: 13) |
| HATF3 | ERKKRRRE (SEQ ID NO: 14) |
| hCT CPP | LGTYTQDFNKTFPQTAIGVGAP (SEQ ID NO: 15) |
| MAP CPP | KLALKLALKALKAALKLA (SEQ ID NO: 16) |
| MPG CPP | GLAFLGFLGAAGSTMGAWSQPKKKRKV (SEQ ID NO: 17) |
| NF-κB | VQRKRQKLMP (SEQ ID NO: 18) |
| OCT-6 | GRKRKKRT (SEQ ID NO: 19) |
| Penetratin CPP | RQIKIWFQNRRMKWKK (SEQ ID NO: 20) |
| Penetratin CPP variant 1 | RQLKLWFQNRRMKWKK (SEQ ID NO: 21) |
| Penetratin CPP variant 2 | REIKIWFQNRRMKWKK (SEQ ID NO: 22) |
| Pep-1 CPP | KETWWETWWTEWSQPKKRKV (SEQ ID NO: 23) |
| pIsl CPP | PVIRVWFQNKRCKDKK (SEQ ID NO: 24) |
| Poly-Arg CPP | RRRRRR(R)$_{1-6}$ (SEQ ID NO: 25) |
| pVEC CPP | LLIILRRRIRKQAHAH (SEQ ID NO: 26) |
| RL-16 CPP | RRLRRLLRRLLRRLRR (SEQ ID NO: 27) |
| RVG CPP | RVGRRRRRRRRR (SEQ ID NO: 28) |
| $R_6W_3$ CPP | RRWWRRWRR (SEQ ID NO: 29) |
| SBP CPP | MGLGLHLLVLAAALQGAWSQPKKKRKV (SEQ ID NO: 30) |
| SV40 | PKKKRKV (SEQ ID NO: 31) |
| SynB1 CPP | RGGRLSYSRRRFSTSTGR (SEQ ID NO: 32) |
| SynB3 CPP | RRLSYSRRRF (SEQ ID NO: 33) |
| SynB5 CPP | RGGRLAYLRRRWAVLGR (SEQ ID NO: 34) |
| Tat$^{47-57}$ CPP | YGRKKRRQRRR (SEQ ID NO: 35) |
| Tat$^{47-56}$ CPP | YGRKKRRQRR (SEQ ID NO: 36) |
| Tat$^{48-56}$ CPP | GRKKRRQRR (SEQ ID NO: 37) |
| Tat$^{48-60}$ CPP | GRKKRRQRRRPPQ (SEQ ID NO: 38) |
| TCF1-α | GKKKKRKREKL (SEQ ID NO: 39) |
| TFIIE-β | SKKKKTKV (SEQ ID NO: 40) |
| TP CPP | GWTLNSAGYLLGKINLKALAALAKKIL (SEQ ID NO: 41) |
| TP10 CPP | AGYLLGKINLKALAALAKKIL (SEQ ID NO: 42) |
| TP2 CPP | PLIYLRLLRGQF (SEQ ID NO: 43) |
| VP22 CPP | DAATATRGRSAASRPTQRPRAPARSASRPRRPVQ (SEQ ID NO: 44) |

Because the function of CPPs depends on their physical characteristics rather than sequence-specific interactions, they can have the reverse sequence as those provided in Table 1 and/or known in the art. Variants of these sequences with one or more amino acid additions, deletions, and/or conservative substitutions that retain the ability to cross cell membranes and/or the BBB are also suitable for use in the invention. The ATF5 polypeptides of the invention can include a cell-penetrating domain having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the exemplary sequences provided in Table 1. The effect of the amino acid addition(s), deletion(s), and/or substitution(s) on the ability of the CPP to mediate cell penetration can be tested using routine methods known in the art.

ATF5 Polypeptides

In one aspect, the invention provides cell-penetrating ATF5 polypeptides having a cell-penetrating region and a truncated ATF5 leucine zipper region, relative to wild-type ATF5. The ATF-5 polypeptides of the invention lack an extended leucine zipper region, such as that which is present in NTAzip-ATF5 (FIG. 1A) and ST-2 (FIG. 1B). As used herein, the terms "extended leucine zipper," "leucine zipper extension," and "enhanced leucine zipper" refer to a peptide having from one to four leucine heptads, i.e., Leu-(X)$_6$ (SEQ ID NO: 45), which sequence is not a wild-type ATF5 leucine zipper sequence. The cell-penetrating ATF5 polypeptides of the invention are capable of crossing a cell membrane, by virtue of their cell-penetrating region, and inhibiting ATF5 activity in the cell. In some embodiments, the cell-penetrating ATF5 polypeptide can cross the BBB. In some embodiments, the ATF5 polypeptide can affect pathways involved in apoptosis. ATF5 activity can be assessed by any of several assays known in the art, including the cell-kill assay described herein. ATF5 activity can also be assessed by its ability to bind to the cAMP-response element (CRE).

The "ATF5 leucine zipper region" is a truncated sequence derived from the wild-type ATF5 leucine zipper region. The term is used to refer only to sequence, and not necessarily to secondary structure. The truncated ATF5 leucine zipper region can have, for example, an amino acid sequence selected from the group consisting of LEGECQGLEARN-RELKERAESV (SEQ ID NO: 7) and LEGECQGLEARN- RELRERAESV (SEQ ID NO: 8). ATF5 polypeptides of the invention include polypeptides consisting essentially of the ATF5 leucine zipper region. Conservative amino acid substitutions are included in the scope of these sequences.

The cell-penetrating region is operably linked to the ATF5 leucine zipper region. In some embodiments, the cell-penetrating region is covalently linked to the ATF5 leucine zipper region, for example, via a peptide bond, a disulfide bond, a thioether bond, or a linker known in the art. Exemplary linkers include, but are not limited to, a substituted alkyl or a substituted cycloalkyl. A cell-penetrating region and an ATF5 leucine zipper region linked directly by an amide bond may be referred to as a "fusion." The cell-penetrating region can be linked to the N-terminus or the C-terminus of the ATF5 leucine zipper region, or via a residue side chain.

Cell-penetrating ATF5 polypeptides of the invention can comprise any combination of cell-penetrating and ATF5 leucine zipper domains disclosed herein. Non-limiting examples of such polypeptides include RQIKIWFQNRRMKWKKLEGECQGLEARNRELKERAESV (SEQ ID NO: 3); RQIKIWFQNRRMKWKKLEGECQGLEARNRELRERAESV (SEQ ID NO: 4); YGRKKRRQRRRLEGECQGLEARNRELKERAESV (SEQ ID NO: 5); and YGRKKRRQRRRLEGECQGLEARNRELRERAESV (SEQ ID NO: 6). In one embodiment, the ATF5 polypeptide is ST-3 (FIG. 1C), having the sequence RQIKIWFQNRRMKWKKLEGECQGLEARNRELKERAESV (SEQ ID NO: 3).

ATF5 polypeptides of the invention include polypeptides having at least about 80%, 81%, 82%, 83%, 84%, 85%, 86%, 87%, 88%, 89%, 90%, 91%, 92%, 93%, 94%, 95%, 96%, 97%, 98%, or 99% identity to those sequences disclosed herein.

ATF5 polypeptides can optionally include an N-terminal acetyl group and/or a C-terminal amide group. ATF5 polypeptides of the invention can optionally include one or more internal cyclizations, such as lactam bridges or hydrocarbon "staples." A lactam bridge is preferably, but not necessarily, created between side chains spaced four amino acid residues apart (BxxxB).

ATF5 polypeptides of the invention can optionally include one or more epitope and/or affinity tags, such as for purification or detection. Non-limiting examples of such tags include FLAG, HA, His, Myc, GST, and the like. ATF5 polypeptides of the invention can optionally include one or more labels.

In certain aspects, the invention provides a composition, e.g., a pharmaceutical composition, comprising an ATF5 polypeptide of the invention, optionally further comprising one or more carriers, diluents, excipients, or other additives. The cell-penetrating ATF5 polypeptides of the invention can be formulation for enteral, parenteral, transdermal, or transmucosal administration, as discussed below. Pharmaceutical compositions can be in numerous dosage forms, for example, tablet, capsule, liquid, solution, softgel, suspension, emulsion, syrup, elixir, tincture, film, powder, ointment, paste, cream, lotion, gel, mousse, foam, lacquer, spray, aerosol, inhaler, nebulizer, ophthalmic drops, patch, suppository, and/or enema.

Also within the scope of the invention are kits comprising the ATF5 polypeptides and compositions as provided herein and, optionally, instructions for use. The kit can further contain at least one additional reagent, and/or one or more additional active agent. Kits typically include a label indicating the intended use of the contents of the kit. The term "label" in this context includes any writing or recorded material supplied on or with the kit, or that otherwise accompanies the kit.

ATF5 polypeptides of the invention can be chemically synthesized, for example, using solid-phase peptide synthesis or solution-phase peptide synthesis, or can be expressed using recombinant methods. Synthesis may occur as fragments of the peptide that are subsequently combined, either chemically or enzymatically. Accordingly, also provided are nucleic acid molecules encoding ATF5 polypeptides of the invention. Such nucleic acids can be constructed by chemical synthesis using an oligonucleotide synthesizer. Nucleic acid molecules of the invention can be designed based on the amino acid sequence of the desired ATF5 polypeptide and selection of those codons that are favored in the host cell in which the recombinant ATF5 polypeptide will be produced. Standard methods can be applied to synthesize a nucleic acid molecule encoding an ATF5 polypeptide of interest.

Once prepared, the nucleic acid encoding a particular ATF5 polypeptide of the invention can be inserted into an expression vector and operably linked to an expression control sequence appropriate for expression of the polypeptide in a desired host or in a target cell, such as a neoplastic cell. In order to obtain high expression levels of the ATF5 polypeptide, the nucleic acid can be operably linked to or associated with transcriptional and translational expression control sequences that are functional in the chosen expression host or target cell.

A wide variety of expression cell/vector combinations can be employed by one skilled in the art. Useful expression vectors for eukaryotic cells include, for example, vectors comprising expression control sequences from SV40, bovine papilloma virus, adenovirus, and cytomegalovirus. Useful expression vectors for bacterial cells include known bacterial plasmids, such as plasmids from *E. coli*, including pCR1, pBR322, pMB9 and their derivatives, wider host range plasmids, such as M13, and filamentous single-stranded DNA phages.

Suitable host cells include prokaryotes, yeast, insect, or higher eukaryotic cells under the control of appropriate promoters. Prokaryotes include gram negative or gram positive organisms, for example *E. coli* or bacilli. Higher eukaryotic cells can be established or cell lines of mammalian origin, examples of which include *Pichia pastoris,* 293 cells, COS-7 cells, L cells, C127 cells, 3T3 cells, Chinese hamster ovary (CHO) cells, HeLa cells, and BHK cells. Cell-free translation systems can also be employed.

III. Methods of Use

The ATF5 polypeptides of the invention can be used to promote cytotoxicity in a neoplastic cell. Cytotoxicity can be measured by known assays, including the cell kill assay described herein. The ATF5 polypeptides of the invention can also be used in methods of treatment, in particular, for the treatment of tumors and hematological malignancies.

Thus, in one aspect, the invention provides a method of treating a solid or liquid tumor in a subject, the method comprising administering to the subject an effective amount of a cell-penetrating ATF5 polypeptide of the invention. The invention also provides a cell-penetrating ATF5 polypeptide for use in treating a solid or liquid tumor. The invention further provides the use of a cell-penetrating ATF5 polypeptide for the manufacture of a medicament for the treatment of a solid or liquid tumor. In some embodiments, the tumor is malignant. In some embodiments, the tumor is a hematological malignancy. In particular, the invention provides a cell-penetrating ATF5 polypeptide for use in treating a hematological malignancy. In addition, the invention provides a method of treating a hematological malignancy in a subject, the method comprising administering to the subject an effective amount of a cell-penetrating ATF5 polypeptide of the invention. In one embodiment, the hematological malignancy is leukemia. In a particular embodiment, the leukemia is acute myelogenous leukemia.

The invention additionally provides a method of promoting cytotoxicity in a neoplastic cell, the method comprising contacting the neoplastic cell with a cell-penetrating ATF5 polypeptide of the invention. Further, the invention provides a cell-penetrating ATF5 polypeptide of the invention for use in promoting cytotoxicity in a neoplastic cell. The invention also provides the use of a cell-penetrating ATF5 polypeptide for the manufacture of a medicament for promoting cytotoxicity in a neoplastic cell.

The invention provides a method of promoting cytotoxicity in a neoplastic cell, the method comprising introducing into a neoplastic cell a nucleic acid molecule encoding an ATF5 polypeptide of the invention. Also provided, is a nucleic acid molecule encoding an ATF5 polypeptide of the invention for use in promoting cytotoxicity in a neoplastic cell. Further provided is the use of a nucleic acid molecule encoding an ATF5 polypeptide of the invention for the manufacture of a medicament for promoting cytotoxicity in a neoplastic cell. In some embodiments, the ATF5 polypeptide comprises a cell-penetrating region. In some embodiments, the ATF5 polypeptide consists essentially of an ATF5 leucine zipper region. In certain embodiments, the ATF5 polypeptide consists essentially of an amino acid sequence selected from the group consisting of LEGECQGLEARN-RELKERAESV (SEQ ID NO: 7) and LEGECQGLEARN-RELRERAESV (SEQ ID NO: 8).

In certain embodiments, the neoplastic cell is in vitro or ex vivo. In some such embodiments, the neoplastic cell can be, for example, a bladder, blood, breast, cervical, colon, endometrial, endothelial, esophageal, gastric, intestinal, kidney, larynx, liver, lung, lymph node, mouth, neural, ovarian, pancreatic, parotid, pharynx, prostate, skin, testicular, tongue, or uterine cell. In some such embodiments, the neoplastic cell can be, for example, a glioma, a medulloblastoma, or a neuroblastoma cell, in particular, an astrocytoma or a glioblastoma cell.

ATF5 has been shown to play a role in promoting radioresistance and malignant phenotypes in A549 human lung adenocarcinoma cells. ATF5-enhanced radioresistance was shown to occur through increased protein expression in the G1-S phase, thereby promoting cell cycle progression and preventing cell senescence. ATF5 was further shown to induce invasiveness of A549 cancer cells by promoting expression of the cell-matrix adhesion protein, integrin β1, through stabilization and also through inhibition of myosin regulatory light chain (MRLC) diphosphorylation (Ishihara et al. 2015). These data suggest that ATF5 functions as one of the key molecules in oncogenic resistance to radiotherapy. Accordingly, in one aspect, the invention provides a method of treating a tumor in a subject comprising administering a cell-penetrating ATF5 polypeptide of the invention in combination with radiation therapy.

A cell-penetrating ATF5 polypeptide of the invention can be administered in combination with one or more additional active agents, for example one or more active agents used to treat cancer. The ATF5 polypeptide and additional active agent(s) can act additively or synergistically. The additional active agent can be a Bcl-2 inhibitor, such as a BH3 mimetic. Non-limiting examples of BH3 mimetics include ABT-263 (Navitoclax), ABT-199 (Venetoclax), S-055746, and PNT-2258. The additional active agent can be one or more chemotherapeutic agents and/or targeted therapeutic agents, including biologic agents. Examples of chemotherapeutic agents include actinomycin, azacitidine, azathioprine, bleomycin, bortezomib, carboplatin, capecitabine, carmustine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, lomustine, mechlorethamine, mercaptopurine, methotrexate, mitoxantrone, oxaliplatin, paclitaxel, pemetrexed, temozolomide, teniposide, tioguanine, topotecan, tretinoin, valrubicin, vinblastine, vincristine, vindesine, and vinorelbine. Examples of targeted therapeutic agents include bevacizumab, pazopanib, poly(ADP-ribose) polymerase (PARP) inhibitors, such as olaparib, tamoxifen, and vintafolide. Combined therapies can be sequential or concurrent.

Administration of the cell-penetrating ATF5 polypeptides of the invention can be via any suitable route determined by the ordinarily skilled artisan. Exemplary routes of administration include enteral, parenteral, transdermal, and transmucosal. Enteral routes involve the alimentary canal, and include oral, sublingual, buccal, and rectal administration. Parenteral routes do not involve the alimentary canal, and may include administration by injection. Examples of parenteral administration include intracerebral, intracranial, intramuscular, intraperitoneal, intrathecal, intratumoral, intravenous, subcutaneous, and ocular. Transdermal administration involves application of the active agent to the skin of the subject. The transmucosal route involves absorption of the active agent by the mucous membranes of the subject, for example, via the nasal, sinus, bronchial (e.g., via inhalation), or vaginal mucosa. Device-mediated administration, such as by osmotic pump, cartridge, or micro pump is also included.

EXAMPLES

Embodiments of the present disclosure can be further defined by reference to the following non-limiting examples. It will be apparent to those skilled in the art that many modifications, both to materials and methods, can be practiced without departing from the scope of the present disclosure.

Example 1. Cytoplasmic and Nuclear Penetration of ST-3 in Glioblastoma Multiforme (GBM) Cells ST-2 (FIG. 1B) is a 67-amino-acid polypeptide containing an N-terminal cell penetrating domain, followed by an engineered leucine zipper extension, and a rat ATF5 bZIP domain truncated after the first valine. It has been demonstrated previously that systemically administered ST-2 can cross the blood-brain barrier, enter cells, and selectively trigger the apoptotic death of neoplastic cells in a mouse glioma model (U.S. Pat. No. 9,758,555). ST-3 (FIG. 1C) is a 38-amino-acid polypeptide containing an N-terminal cell penetrating domain, followed by the human ATF5 bZIP domain truncated after the first valine. Prior to the present invention, the leucine zipper extension region, which ST-2 contains and ST-3 lacks, was thought to be required for activity of the molecule.

All cellular penetration assays were performed in U251 cells. Immunofluorescence detection of ST-3 in U251 cells allow for quantitation of cellular and nuclear penetration.

U251 cells were seeded at a density of 5×10³ in a 96-well plate and cultured at 37° C. in 5% $CO_2$. At approximately 12-24 hours post-seeding, U251 cells were treated with ST-3 (or ST-2) for 1-4 hours. Following extensive washing in PBS, cells were fixed in 1% formaldehyde for 15 minutes at room temperature (RT), permeabilized with 0.1% Triton-X-100 for 15 minutes at RT, and blocked with 1% BSA in PBS for 30 minutes at RT. Fixed cells were incubated with SPTX-001 rabbit polyclonal anti-ST-3 antibody (1:2000 dilution) overnight at 4° C. or for 90 minutes at RT, followed by incubation with FITC-conjugated goat ant-rabbit secondary antibody (1:500-5000 dilution) for 45-60 minutes at RT. Nuclei were visualized using DAPI staining (2.85 µg/mL) for 15 minutes at RT. ST-3-positive cells were measured by a CompuCyte iCys scanning cytometer with four-color analysis. Analysis supported gating a quantification of ST-3-positive population.

ST-3 (100 µM) penetrated 100% of cytoplasmic membranes and about 84% of nuclear membranes in U251 cells after a 1-hour incubation (FIG. 2).

Example 2. Evaluation of ST-3 Activity In Vitro

Effects of ST-3 on HL60 Promyelocytic Leukemia (PML) Cells and U251 GBM Cells

HL60 PML suspension cells were set at a density of 3.5×10³ cells/well in 150 µL of RPMI+1.5% fetal bovine serum (FBS) in a 96 well dish. ST-3, reconstituted at a concentration of 10 mg/mL in 20 mM His, pH 7.5, was added to each well at a volume of 50 µL to a final concentration range of 0-80 µM. Cells were incubated with ST-3 for 48 hours at 37° C. Cell viability was quantified by flow cytometry using an Annexin V FITC apoptosis detection kit from Abcam. Briefly, cells were washed with PBS and resuspended in 1× assay buffer containing Annexin V FITC and propidium iodide (PI). Annexin V detects apoptotic cells, and PI stains dead cells. After staining, apoptotic cells show green fluorescence, dead cells show red and green fluorescence, and live cells show little or no fluorescence. Cells were selected for analysis based on forward scatter (FSC) vs. side scatter (SSC), and analyzed by BD Accuri C6 Plus flow cytometer to detect Annexin V-FITC binding (Ex=488 nm; Em=530 nm) using FITC signal detector and PI staining by the phycoerythrin emission signal detector. Percentage of Annexin $V^{low}$ and $PI^{low}$ were quantified and presented as % Viability. $EC_{50}$ values were calculated using GraphPad Prism v.7 XML.

Alternatively, adherent U251 or U87 cells were set at a density of 3.5×10³ cells/well in 150 µL of media on day −1. On day 0, media was removed and replenished with 150 µL of fresh media, and cells were treated with ST-3 as described. Following 48-hour incubation at 37° C., floating cells were collected, adherent cells were washed with Dulbecco's Phosphate Buffered Saline (DPBS), dissociated from the dish with 50 µL 2.5% trypsin at room temperature, and combined with floating cells. Cell viability was determined as described above for suspension cells.

Figure 3A:
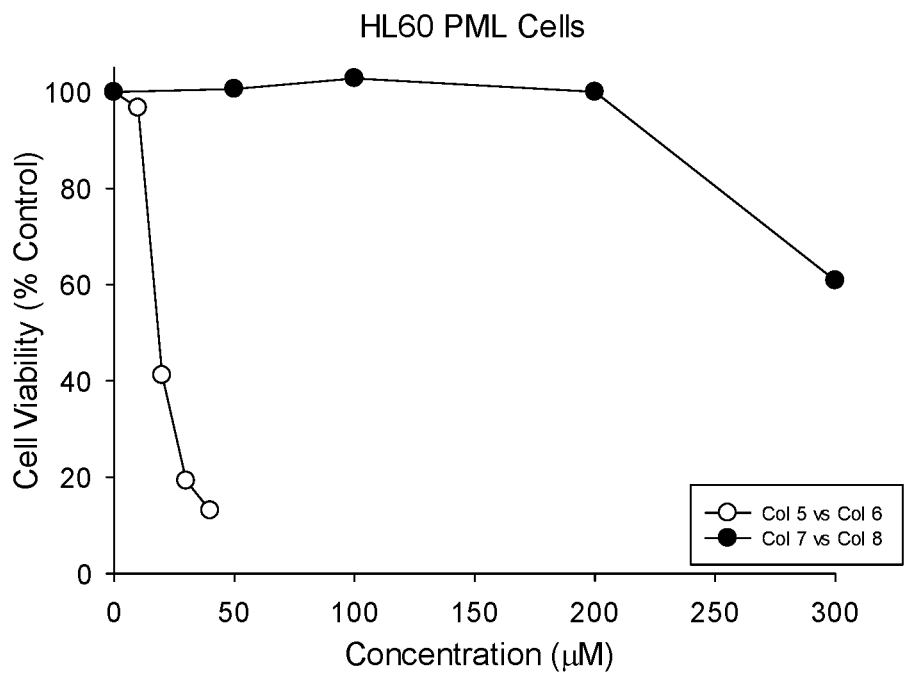
Figure 3B:
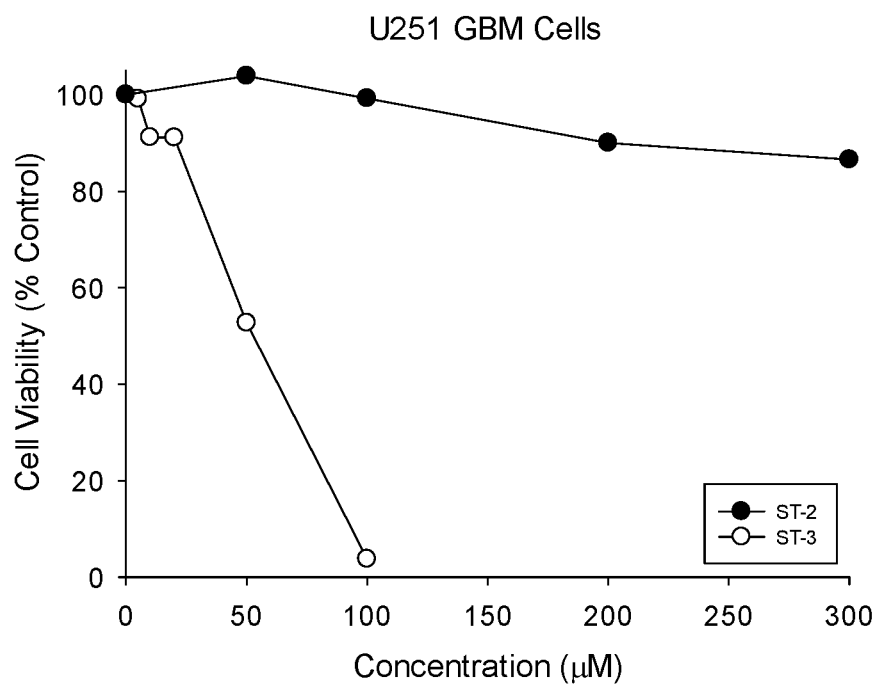

Compared to ST-2, ST-3 surprisingly demonstrates superior in vitro potency in HL60 PML cells (FIG. 3A) and in U251 GBM cells (FIG. 3B).

Effects of ST-3 on T98G GBM Cells

T98G cells were set at a density of 2×10³/well in 200 µL of RPMI+1.5% fetal bovine serum (FBS) in black-walled Nunc™ MicroWell™ 96-Well Optical-Bottom Plates with Polymer Base.

On day −1, adherent T98G cells were washed of complete media (RPMI+10% FBS) with 6 mL Dulbecco's Phosphate Buffered Saline (DPBS), and dissociated from T25 Nunclon™ Delta flask with 2 mL trypsin at room temperature. Trypsin was quenched with 6 mL complete media, and cells were resuspended in fresh complete media at a concentration of 1×10⁶ cells/mL. Cells were then adjusted to a concentration of 1×10⁴ cells/mL in RPMI+1.5% FBS, and 200 µL of culture was added to each well (B2 to G11) of a Nunc™ 96-well Flat Bottom Black Polystyrol Clear Bottom plate to a final cell concentration of 2×10³ cells/well. Cells were set in an incubator at 37° C. and 5% $CO_2$ with humidity for 24 hours.

On day 0, 100 µL of media was removed from each well. Lyophilized ST-3, freshly reconstituted in Tris Buffer (20 mM Tris+150 mM NaCl+0.05% Polysorbate-20, at pH 8.0) to stock solution of 5 mg/mL, was added to each well at a volume of 100 µL and a final concentration range of 0-526 µM. Cells were incubated with ST-3 for 72 hours prior to quantifying cell viability.

On day 3, media was removed from wells, and wells were washed with 100 µL DPBS. Cells were resuspended in 100 µL RPMI+10% FBS. CellTiter-Blue® Cell Viability Assay (Promega Corp., Madison, Wis.) was performed by adding 20 µL of CellTiter-Blue® reagent to each well. Plates were returned to the incubator at 37° C. and 5% $CO_2$ with humidity for 1.5-2 hours. CellTiter-Blue® assay results were read by Eppendorf PlateReader AF2200 at Ex. 535 nm/Em. 595 nm according to manufacturer's instructions. Data is presented as % Viability. Cell viability was calculated as (Sample value/Buffer control value)×100. $EC_{50}$ values were calculated using GraphPad Prism v.7 XML.

ST-3 induced complete loss of cell viability, indicated by loss of conversion of the redox dye resazurin into the fluorescent end product resorufin by viable cells. An $EC_{50}$ value of 69.0 µM was calculated for ST-3. Results are shown in FIG. 3C. The extensive cell kill observed at higher concentrations of ST-3 indicates unexpectedly superior cytotoxic activity over ST-2 in vitro.

This Example demonstrates that the human ATF5 bZIP domain fused to the Penetratin domain for cell entry (ST-3), is sufficient to for cytotoxic activity in glioblastoma, neuroblastoma, and leukemia cells, and is more potent than ST-2. A summary of the results is shown in Table 2.

TABLE 2

| $EC_{50}$ (µM) of ATF-5-Derived Polypeptides in Cancer Cells | | | | |
|---|---|---|---|---|
| | HL60 | U251 | T98G | U87 |
| ST-2 | >200 | >200 | >200 | >200 |
| ST-3 | 16 | 42 | 69 | 45 |

Example 3. Evaluation of ST-3+ABT-263 in U87 Glioblastoma Caspase Activation Assay Activation of caspase enzymes occurs in the early stages of apoptosis. In this Example, we investigated the effect on caspase activation of ST-3 in combination with the Bcl-2 inhibitor ABT-263 (Navitoclax). U87 cells were prepared as described in Example 2 for T98G cells. Lyophilized ST-3 was freshly reconstituted in Tris Buffer at a concentration of 5 mg/mL, and adjusted to a working concentration of 200 µM. ST-3 was added to cells in 100 µL Tris Buffer at a final concentration range of 0-20 µM. ABT-263 (Selleck Chem, Houston, Tex.) was reconstituted in DMSO to a concentration of 500 µM (final DMSO concentration was 1%).

On day 0, 100 μL of media was removed from each well, followed by addition of 98 μL of ST-3 in Tris Buffer and 2 μL of ABT-263 solution (final concentration of 0.5 μM) or DMSO control to each well. Alternatively, cells were exposed to staurosporine as positive control (10 μM).

On day 3, media was removed from wells, and wells were washed with 100 μL DPBS. Cells were resuspended in 100 μL RPMI+10% FBS. Apo-ONE® Homogenous Caspase 3/7 Activity Assay (Promega Corp., Madison, Wis.) was performed by adding 100 of Apo-ONE® reagent to each well. Plates were incubated at ambient temperature in the dark for 1.5-2 hours. Fluorescence was recorded by Eppendorf PlateReader AF2200 at Ex. 485 nm/Em. 527 nm. Data is presented as % Caspase Activity of positive control (staurosporine 10 μM). Caspase activity was calculated as (Sample value/Positive control value)×100.

Figure 4:
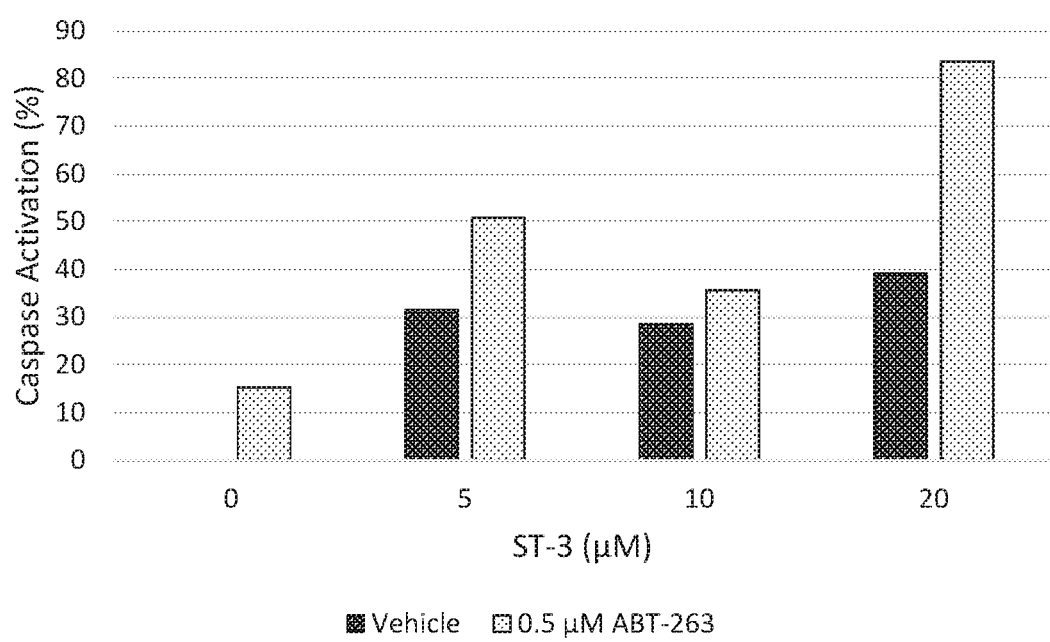
FIG. 4 shows that ST-3 caspase activation is enhanced in the presence of ABT-263. Caspase activation was assessed after 24 hours of drug exposure.

Results indicate that ST-3 alone resulted in an increase in caspase 3/7 activity, induced by 24-hour incubation with staurosporine (10 to 28.5-38.9% of maximal response. Caspase 3/7 activity increased from 15.5% with ABT-263 alone, to 50.7%, 35.7%, and 83.6% of maximal response when ST-3 was administered at 5, 10, and 20 respectively, in combination with 0.5 μM ABT-263. Results are shown in Table 3 and FIG. 4.

TABLE 3

| Conc. of ST-3 (μM) | % Caspase Activation | |
|---|---|---|
| | ST-3 alone | ST-3 + ABT-263 |
| 0 | 0 | 15.32 |
| 5 | 31.48 | 50.76 |
| 10 | 28.58 | 35.74 |
| 20 | 39.11 | 83.60 |
| Positive Control | 100 | 100 |

These data indicate that combination of ST-3 with ABT-263 results in enhanced activity compared to either single agent alone.

Example 4. In Vitro Activity of ST-3 Containing Lactam Bridges

We made and tested ST-3 molecules having a lactam bridge between amino acid side chains. Positions of the bridges are shown in Table 4.

TABLE 4

| Molecule | Modification(s) |
|---|---|
| ST-3-A | K13-E20 bridge |
| ST-3-B | E25-RΔK29 bridge |
| ST-3-C | AΔK26-E30 bridge |
| ST-3-D | E33-SΔK37 bridge |

Figure 5:
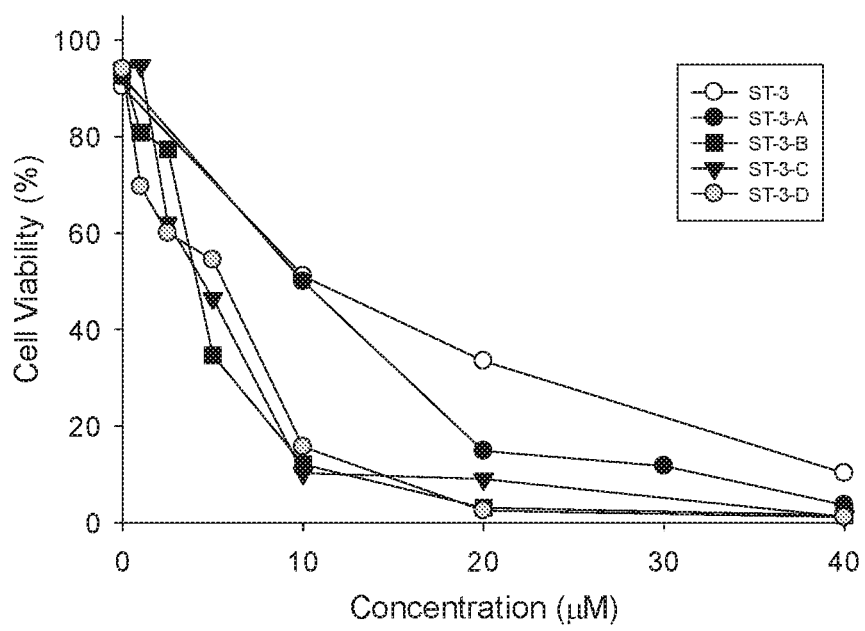
FIG. 5 shows cytotoxic activity of ST-3 molecules comprising a lactam bridge between K13 and E20 (ST-3-A), between E25 and RΔK29 (ST-3-B), between AΔK26 and E30 (ST-3-C), or between E33 and SΔK37 (ST-3-D).

The Annexin V/PI cell viability assay described in Example 2 was used to measure cytotoxicity in HL60 cells. Addition of a lactam bridge improved activity of ST-3 (FIG. 5).

Example 5. In Vitro Activity of ATF5 Polypeptide with Tat CPP

We tested an ATF5 polypeptide having a Tat-derived cell penetration domain (SEQ ID NO: 36) fused to the ST-3 bZIP domain (SEQ ID NO: 7) in the HL-60 cell viability assay described in Example 2. This ATF5 polypeptide has cytotoxic activity, as shown in Table 5.

TABLE 5

| Concentration (μM) | % Viability |
|---|---|
| 0 | 92.4 |
| 10 | 81.9 |
| 20 | 66.4 |
| 30 | 62.1 |
| 40 | 54.4 |

Example 6. In Vivo Activity of ST-3

Figure 6A:
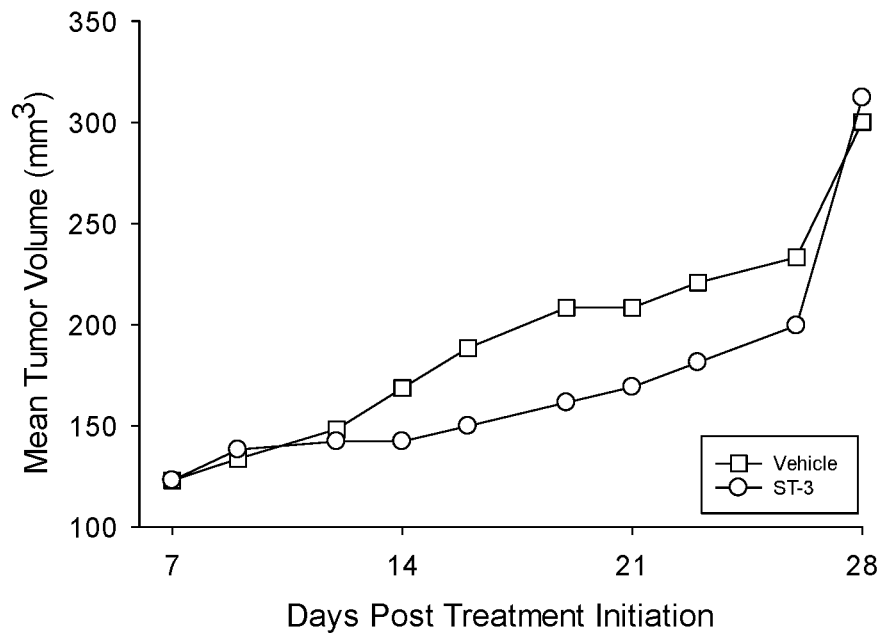
FIG. 6A-6C show in vivo activity of ST-3.

In this Example, we show that ST-3 affects tumor growth in multiple subcutaneous tumor models. In the first experiment, $5 \times 10^6$ U87 MG-Luc glioblastoma cells (MI Bioresearch) were implanted into the axilla of Nu/Nu mice. Tumors were grown to a volume of 100-200 mm³. ST-3 was administered at a dose of 50 mg/kg via intraperitoneal (IP) injection. The injection schedule was (QDx5, 2off)×3, followed by (Q3Dx2, 3off)×3. ST-3 treatment resulted in modest repression of tumor growth for approximately 3 weeks (FIG. 6A).

In addition, we compared systemic administration of ST-3 via IP injection with local administration via intratumoral (IT) injection. Subcutaneous U251 xenografts were implanted in Nu/Nu mice and grown to a volume of 100-150 mm³. ST-3 was administered Q3D at a dose of 25 mg/kg via IP or IT injection. Tumors were excised 24 hours after the final treatment and processed for H&E and for TUNEL staining to detect apoptosis. Images were viewed by a pathologist and lesions were quantified. Results showed that ST-3 induced apoptosis in the subcutaneous tumor xenograft via both systemic and local administration (Table 6).

TABLE 6

| Treatment | Route of Admin. | TUNEL⁺ Foci <1 mm | TUNEL⁺ Foci >1 mm |
|---|---|---|---|
| Vehicle | IP | 0.5 | 1 |
| ST-3 | IP | 6 | 0.5 |
| Vehicle | IT | 1.5 | 1 |
| ST-3 | IT | 1 | 2.5* |

*Foci measured 3-4 mm.

Figure 6B:
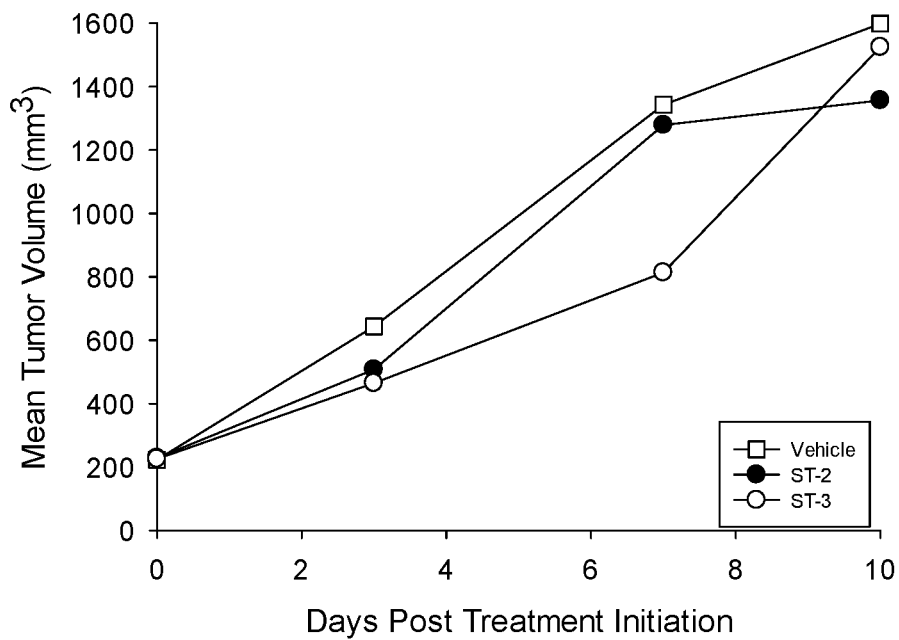

To assess the in vivo effects of ST-3 on human tumor cells, we used a patient-derived xenograft model. Briefly, adult mesenchymal GBM tumors were passaged in mice via subcutaneous implantation into the flank. Treatment was initiated approximately 14 days post-implant. Mice were administered a dose of 25 mg/kg ST-3 or ST-2 IT once daily for 8 days. ST-3 delayed tumor growth better than ST-2 (FIG. 6B). Due to the aggressive nature of these tumors, a 3-7 day treatment benefit is considered substantial.

Figure 6C:
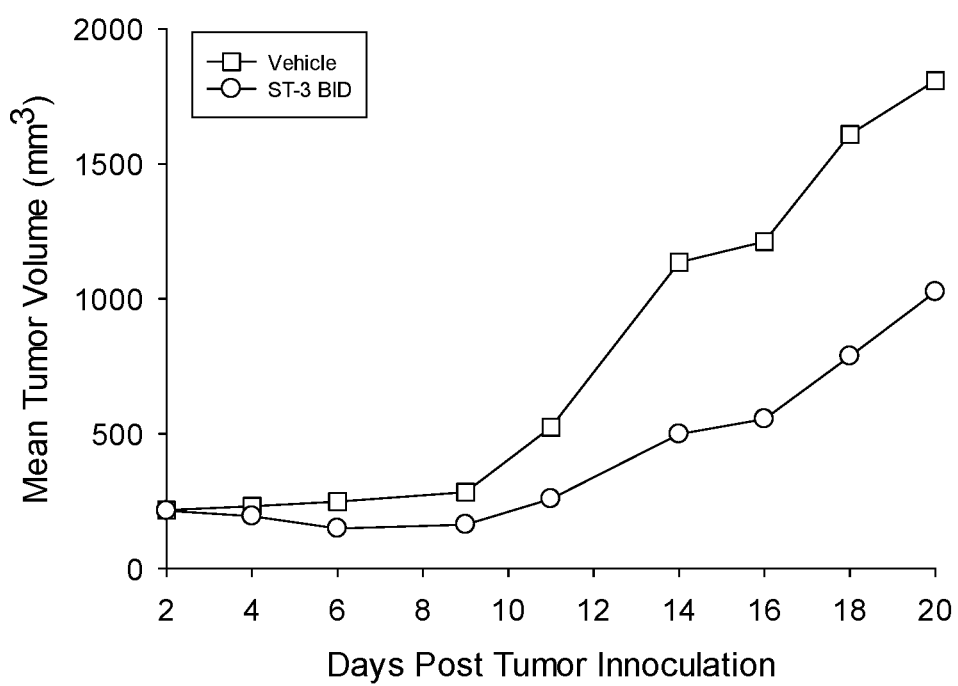

We also evaluated the in vivo effects of ST-3 in an HL-60 subcutaneous tumor model. Briefly, $5 \times 10^6$ HL-60 human promyelocytic leukemia cells suspended in 1:1 RPMI:Matrigel were injected via subcutaneous injection into the axilla of nu/nu mice. Beginning on day 2 following tumor inoculation, the ATF5 polypeptide was administered by subcutaneous injection at a dose of 25 mg/kg BID for 21 days. Tumor volume (FIG. 6C) was determined over the course of the experiment.

REFERENCES

Acharya A, et al. Experimental identification of homodimerizing B-ZIP families in *Homo sapiens. J. Struct. Biol.* 155:130-139 (2006).

Alves I D, et al. Membrane interaction and perturbation mechanisms induced by two cationic cell penetrating peptides with distinct charge distribution. *Biochim. Biophys. Acta* 1780:948-959 (2008).

Angelastro J M, et al. Regulated expression of ATF5 is required for the progression of neural progenitor cells to neurons. *J. Neurosci.* 23:4590-4600 (2003).

Arias A, et al. Regulated ATF5 loss-of-function in adult mice blocks formation and causes regression/eradication of gliomas. *Oncogene* 31:739-751 (2012).

Brodsky J L, et al. Translocation of proteins across the endoplasmic reticulum membrane. *Int. Rev. Cyt.* 178:277-328 (1998).

Chaloin L, et al. Conformations of primary amphipathic carrier peptides in membrane mimicking environments. *Biochem.* 36:11179-11187 (1997).

Chaloin L, et al. Design of carrier peptide-oligonucleotide conjugates with rapid membrane translocation and nuclear localization properties. *Biochem. Biophys. Res. Commun.* 243:601-608 (1998).

Chen A, et al. ATF5 is overexpressed in epithelial ovarian carcinomas and interference with its function increases apoptosis through the downregulation of Bcl-2 in SKOV-3 cells. *Int. J. Gynecol. Pathol.* 31:532-537 (2012).

Crombez L, et al. A new potent secondary amphipathic cell-penetrating peptide for siRNA delivery into mammalian cells. *Mol. Ther. J. Am. Soc. Gene Ther.* 17:95-103 (2009).

Cruz J, et al. A membrane-translocating peptide penetrates into bilayers without significant bilayer perturbations. *Biophys. J.* 104:2419-2428 (2013).

Derossi D, et al. Trojan peptides: the penetratin system for intracellular delivery. *Trends Cell Biol.* 8:84-87 (1998).

Elliott G, et al. Intercellular trafficking and protein delivery by a Herpesvirus structural protein. *Cell* 88:223-233 (1997).

Elmquist A, et al. VE-cadherin-derived cell-penetrating peptide, pVEC, with carrier functions. *Exp. Cell Res.* 269:237-244 (2001).

Futaki S, et al. Arginine-rich peptides. An abundant source of membrane-permeable peptides having potential as carriers for intracellular protein delivery. *J. Biol. Chem.* 276:5836-5840 (2001).

Gautam A, et al. CPPsite: a curated database of cell penetrating peptides. Database doi:10.1093/database/bas015 (2012).

Greene L A, et al. The transcription factor ATF5: role in neurodevelopment and neural tumors. *J. Neurochem.* 108:11-22 (2009).

Hällbrink M, et al. Cargo delivery kinetics of cell-penetrating peptides. *Biochim. Biophys. Acta* 1515:101-109 (2001).

Heitz F, et al. Twenty years of cell-penetrating peptides: from molecular mechanisms to therapeutics. *Brit. J. Pharmacol.* 157:195-206 (2009).

Hervé F, et al. CNS delivery via adsorptive transcytosis. *AAPS J.* 10:455-472 (2008).

Ishihara S, et al. Activating transcription factor 5 enhances radioresistance and malignancy in cancer cells. *Oncotarget.* 6:4602-14 (2015).

Jo, D, et al. Intracellular protein therapy with SOCS3 inhibits inflammation and apoptosis. *Nat. Med.* 11:892-898 (2005).

Karpel-Massler G, et al. A Synthetic Cell-Penetrating Dominant-Negative ATF5 Peptide Exerts Anticancer Activity against a Broad Spectrum of Treatment-Resistant Cancers. *Clin. Cancer Res.* 22:4698-4711 (2016).

Kilk K, et al. Cellular internalization of a cargo complex with a novel peptide derived from the third helix of the islet-1 homeodomain. Comparison with the penetratin peptide. *Bioconjug. Chem.* 12:911-916 (2001).

Krautwald S, et al. Inhibition of regulated cell death by cell-penetrating peptides. *Cell. Mol. Life Sci.* 73:2269-2284 (2016).

Krylov D, et al. Extending dimerization interfaces: the bZIP basic region can form a coiled-coil. *EMBO J.* 14:5329-5337 (1995).

Kumar P, et al. Transvascular delivery of small interfering RNA to the central nervous system. *Nature* 448:39-43 (2007).

Kwon S-J, et al. Transduction of the MPG-tagged fusion protein into mammalian cells and oocytes depends on amiloride-sensitive endocytic pathway. *BMC Biotechnol.* 9:73-84 (2009).

Lindgren M, et al. Cell-penetrating peptides. *Trends Pharmacol. Sci.* 21:99-103 (2000).

Lundberg P, et al. Delivery of short interfering RNA using endosomolytic cell-penetrating peptides. *FASEB J.* 21:2664-2671 (2007).

Magzoub M, et al. Interaction and structure induction of cell-penetrating peptides in the presence of phospholipid vesicles. *Biochim. Biophys. Acta* 1512:77-89 (2001).

Mitchell D J, et al. Polyarginine enters cells more efficiently than other polycationic homopolymers. *J. Pept. Res.* 56:318-325 (2000).

Moll J R, et al. Attractive interhelical electrostatic interactions in the proline- and acidic-rich region (PAR) leucine zipper subfamily preclude heterodimerization with other basic leucine zipper subfamilies. *J. Biol. Chem.* 275:34826-34832 (2000).

Monaco S E, et al. The transcription factor ATF5 is widely expressed in carcinomas, and interference with its function selectively kills neoplastic, but not nontransformed, breast cell lines. *Int. J. Cancer* 120:1883-1890 (2007).

Morris M C, et al. A new peptide vector for efficient delivery of oligonucleotides into mammalian cells. *Nucleic Acids Res.* 25:2730-2736 (1997).

Morris M C, et al. A peptide carrier for the delivery of biologically active proteins into mammalian cells. *Nat. Biotechnol.* 19:1173-1176 (2001).

Muñoz-Morris M A et al. The peptide carrier Pep-1 forms biologically efficient nanoparticle complexes. *Biochem. Biophys. Res. Commun.* 355:877-882 (2007).

Munyendo W L L, et al. Cell penetrating peptides in the delivery of biopharmaceuticals. *Biomolecules* 2:187-202 (2012).

Oehlke J, et al. Cellular uptake of an alpha-helical amphipathic model peptide with the potential to deliver polar compounds into the cell interior non-endocytically. *Biochim. Biophys. Acta* 1414:127-139 (1998).

Olive M, et al. A dominant negative activation protein-1 (AP1) that abolishes DNA binding and inhibits oncogenesis. *J. Biol. Chem.* 272:18586-18594 (1997).

Pooga M, et al. Cell penetration by transportan. *FASEB J.* 12:67-77 (1998).

Ragin A. D. et al. Cellular Import Mediated by Nuclear Localization Signal Peptide Sequences. *Chemist and Biology.* 8:943-948 (2002).

Rousselle C, et al. Enhanced delivery of doxorubicin into the brain via a peptide-vector-mediated strategy: saturation kinetics and specificity. *J. Pharmacol. Exp. Ther.* 296:124-131 (2001).

Scheller A, et al. Structural requirements for cellular uptake of alpha-helical amphipathic peptides. *J. Peptide Sci.* 5:185-194 (1999).

Schmidt M C, et al. Translocation of human calcitonin in respiratory nasal epithelium is associated with self assembly in lipid membrane. *Biochem.* 37:16582-16590 (1998).

Sheng, Z, et al. An activating transcription factor 5-mediated survival pathway as a target for cancer therapy? *Oncotarget.* 1:457-460 (2010a).

Sheng Z, et al. A genome-wide RNA interference screen reveals an essential CREB3L2-ATF5-MCL1 survival pathway in malignant glioma with therapeutic implications. *Nat. Med.* 16:671-677 (2010b).

Soomets U, et al. Deletion analogues of transportan. *Biochim. Biophys Acta* 1467:165-176 (2000).

Suzuki T, et al. Possible existence of common internalization mechanisms among arginine-rich peptides. *J. Biol. Chem.* 277:2437-2443 (2002).

Thorén PEG, et al. The Antennapedia peptide penetratin translocates across lipid bilayers—the first direct observation. *FEBS Lett.* 482:265-68 (2000).

Vivès E, et al. A truncated HIV-1 Tat protein basic domain rapidly translocates through the plasma membrane and accumulates in the cell nucleus. *J. Biol. Chem.* 272: 16010-16017 (1997).

Wender P A, et al. The design, synthesis, and evaluation of molecules that enable or enhance cellular uptake: peptoid molecular transporters. *Proc. Natl. Acad. Sci. U.S.A.* 97:13003-13008 (2000).

Zhao Y, et al. Chemical engineering of cell penetrating antibodies. *J. Immunol. Methods* 254:137-45 (2001).

Zou L L, et al. Cell-penetrating peptide-mediated therapeutic molecule delivery into the central nervous system. *Curr. Neuropharmacol.* 11:197-208 (2013).

The present invention is further described by the following claims.

The invention claimed is:

1. A cell-penetrating ATF5 polypeptide consisting essentially of a cell-penetrating region and an ATF5 leucine zipper region, wherein the ATF5 leucine zipper region has an amino acid sequence selected from the group consisting of LEGECQGLEARNRELKERAESV (SEQ ID NO: 7) and LEGECQGLEARNRELRERAESV (SEQ ID NO: 8), and wherein the polypeptide lacks an extended leucine zipper region.

2. The cell-penetrating ATF5 polypeptide according to claim 1, wherein the polypeptide comprises a lactam bridge between positions of SEQ ID NO: 7 or SEQ ID NO: 8 selected from the group consisting of:
(a) E9 and RΔK13;
(b) AΔK10 and E14; and
(c) E17 and SΔK21.

3. The cell-penetrating ATF5 polypeptide according to claim 1, wherein the cell-penetrating region has an amino acid sequence selected from the group consisting of: RQIKIWFQNRRMKWKK (SEQ ID NO: 20), RQLKLWFQNRRMKWKK (SEQ ID NO: 21), YGRKKRRQRRR (SEQ ID NO: 35), and YGRKKRRQRR (SEQ ID NO: 36).

4. The cell-penetrating ATF5 polypeptide according to claim 1, wherein the polypeptide comprises an N-terminal acetyl group and/or a C-terminal amide group.

5. The cell-penetrating ATF5 polypeptide according to claim 1, which is capable of crossing the blood-brain barrier.

6. A composition comprising the cell-penetrating ATF5 polypeptide according to claim 1.

7. The composition according to claim 6, which is a pharmaceutical composition.

8. A kit comprising the cell-penetrating ATF5 polypeptide according claim 1.

9. An in vitro or ex vivo method of promoting cytotoxicity in a neoplastic cell, the method comprising contacting the neoplastic cell with the cell-penetrating ATF5 polypeptide according to claim 1.

10. A cell-penetrating ATF5 polypeptide comprising an amino acid sequence selected from the group consisting of:

```
                                       (SEQ ID NO: 3)
RQIKIWFQNRRMKWKKLEGECQGLEARNRELKERAESV;

(SEQ ID NO: 4)
RQIKIWFQNRRMKWKKLEGECQGLEARNRELRERAESV;

(SEQ ID NO: 5)
YGRKKRRQRRRLEGECQGLEARNRELKERAESV;
and
```

```
                                       (SEQ ID NO: 6)
YGRKKRRQRRRLEGECQGLEARNRELRERAESV.
``` wherein the polypeptide lacks an extended leucine zipper region.

11. The cell-penetrating ATF5 polypeptide according to claim 10, comprising the amino acid sequence RQIKIWFQNRRMKWKKLEGECQGLEARNRELKERAESV (SEQ ID NO: 3).

12. The cell-penetrating ATF5 polypeptide according to claim 11, wherein the polypeptide comprises a lactam bridge at between positions selected from the group consisting of:
(a) K13 and E20;
(b) E25 and RΔK29;
(c) AΔK26 and E30; and
(d) E33 and SΔK37.

13. The cell-penetrating ATF5 polypeptide according to claim 10, wherein the polypeptide comprises an N-terminal acetyl group and/or a C-terminal amide group.

14. The cell-penetrating ATF5 polypeptide according to claim 10, which is capable of crossing the blood-brain barrier.

15. A composition comprising the cell-penetrating ATF5 polypeptide according to claim 10.

16. The composition according to claim 15, which is a pharmaceutical composition.

17. A kit comprising the cell-penetrating ATF5 polypeptide according to claim 10.

18. An in vitro or ex vivo method of promoting cytotoxicity in a neoplastic cell, the method comprising contacting the neoplastic cell with the cell-penetrating ATF5 polypeptide according to claim 10.

19. An in vitro or ex vivo method of promoting cytotoxicity in a neoplastic cell, the method comprising introducing into the neoplastic cell an ATF5 polypeptide consisting essentially of an amino acid sequence selected from the group consisting of LEGECQGLEARNRELKERAESV (SEQ ID NO: 7) and LEGECQGLEARNRELRERAESV (SEQ ID NO: 8), wherein the polypeptide lacks an extended leucine zipper region.

20. An in vitro or ex vivo method of promoting cytotoxicity in a neoplastic cell, the method comprising introducing into the neoplastic cell a nucleic acid molecule encoding an ATF5 polypeptide consisting essentially of an amino acid sequence selected from the group consisting of LEGECQGLEARNRELKERAESV (SEQ ID NO: 7) and LEGECQGLEARNRELRERAESV (SEQ ID NO: 8), wherein the polypeptide lacks an extended leucine zipper region.

* * * * *

SEQUENCE LISTING

```
<160> NUMBER OF SEQ ID NOS: 45

<210> SEQ ID NO 1
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Glu Gln Arg Ala Glu Glu Leu Ala Arg Glu Asn Glu Glu Leu Leu
1               5                   10                  15

Glu Lys Glu Ala Glu Glu Leu Glu Gln Glu Asn Ala Glu Leu Glu Gly
            20                  25                  30

Glu Cys Gln Gly Leu Glu Ala Arg Asn Arg Glu Leu Arg Glu Arg Ala
        35                  40                  45

Glu Ser Val Glu Arg Glu Ile Gln Tyr Val Lys Asp Leu Leu Ile Glu
    50                  55                  60

Val Tyr Lys Ala Arg Ser Gln Arg Thr Arg Ser Ala
65                  70                  75

<210> SEQ ID NO 2
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Gln Ile Lys Ile Trp Phe Gln Asn Arg Arg Met Lys Trp Lys Lys
1               5                   10                  15

Leu Glu Gln Arg Ala Glu Glu Leu Ala Arg Glu Asn Glu Glu Leu Leu
            20                  25                  30

Glu Lys Glu Ala Glu Glu Leu Glu Gln Glu Asn Ala Glu Leu Glu Gly
        35                  40                  45

Glu Cys Gln Gly Leu Glu Ala Arg Asn Arg Glu Leu Arg Glu Arg Ala
    50                  55                  60

Glu Ser Val
65

<210> SEQ ID NO 3
```

```
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Arg Gln Ile Lys Ile Trp Phe Gln Asn Arg Arg Met Lys Trp Lys Lys
1               5                   10                  15

Leu Glu Gly Glu Cys Gln Gly Leu Glu Ala Arg Asn Arg Glu Leu Lys
            20                  25                  30

Glu Arg Ala Glu Ser Val
        35

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Gln Ile Lys Ile Trp Phe Gln Asn Arg Arg Met Lys Trp Lys Lys
1               5                   10                  15

Leu Glu Gly Glu Cys Gln Gly Leu Glu Ala Arg Asn Arg Glu Leu Arg
            20                  25                  30

Glu Arg Ala Glu Ser Val
        35

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Tyr Gly Arg Lys Lys Arg Arg Gln Arg Arg Leu Glu Gly Glu Cys
1               5                   10                  15

Gln Gly Leu Glu Ala Arg Asn Arg Glu Leu Lys Glu Arg Ala Glu Ser
            20                  25                  30

Val

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Tyr Gly Arg Lys Lys Arg Arg Gln Arg Arg Leu Glu Gly Glu Cys
1               5                   10                  15

Gln Gly Leu Glu Ala Arg Asn Arg Glu Leu Arg Glu Arg Ala Glu Ser
            20                  25                  30

Val

<210> SEQ ID NO 7
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Glu Gly Glu Cys Gln Gly Leu Glu Ala Arg Asn Arg Glu Leu Lys
1               5                   10                  15

Glu Arg Ala Glu Ser Val
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Glu Gly Glu Cys Gln Gly Leu Glu Ala Arg Asn Arg Glu Leu Arg
1               5                   10                  15

Glu Arg Ala Glu Ser Val
            20

<210> SEQ ID NO 9
<211> LENGTH: 7
<212> TYPE: PRT
<213> ORGANISM: Caenorhabditis elegans

<400> SEQUENCE: 9

Phe Lys Lys Phe Arg Lys Phe
1               5

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Leu Trp Arg Ala Leu Trp Arg Leu Leu Arg Ser Leu Trp Arg Leu
1               5                   10                  15

Leu Trp Lys

<210> SEQ ID NO 11
<211> LENGTH: 23
<212> TYPE: PRT
<213> ORGANISM: Drosophila sp.

<400> SEQUENCE: 11

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 12

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 13
<211> LENGTH: 16
<212> TYPE: PRT
<213> ORGANISM: Unknown
<220> FEATURE:
<223> OTHER INFORMATION: Description of Unknown:
      FGF4 CPP sequence

<400> SEQUENCE: 13

Ala Ala Val Ala Leu Leu Pro Ala Val Leu Leu Ala Leu Leu Ala Pro
1               5                   10                  15

<210> SEQ ID NO 14
<211> LENGTH: 8
<212> TYPE: PRT
<213> ORGANISM: Homo sapiens

<400> SEQUENCE: 14

Glu Arg Lys Lys Arg Arg Arg Glu
1               5

<210> SEQ ID NO 15
<211> LENGTH: 22
<212> TYPE: PRT
<213> ORGANISM: Homo sapiens

<400> SEQUENCE: 15

Leu Gly Thr Tyr Thr Gln Asp Phe Asn Lys Thr Phe Pro Gln Thr Ala
1               5                   10                  15

Ile Gly Val Gly Ala Pro
            20

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Leu Ala Leu Lys Leu Ala Leu Lys Ala Leu Lys Ala Ala Leu Lys
1               5                   10                  15

Leu Ala

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Leu Ala Phe Leu Gly Phe Leu Gly Ala Ala Gly Ser Thr Met Gly
1               5                   10                  15

```
Ala Trp Ser Gln Pro Lys Lys Arg Lys Val
            20                  25
```

<210> SEQ ID NO 18
<211> LENGTH: 10
<212> TYPE: PRT
<213> ORGANISM: Unknown
<220> FEATURE:
<223> OTHER INFORMATION: Description of Unknown:
      NF-kappaB sequence

<400> SEQUENCE: 18

```
Val Gln Arg Lys Arg Gln Lys Leu Met Pro
1               5                   10
```

<210> SEQ ID NO 19
<211> LENGTH: 8
<212> TYPE: PRT
<213> ORGANISM: Unknown
<220> FEATURE:
<223> OTHER INFORMATION: Description of Unknown:
      OCT-6 sequence

<400> SEQUENCE: 19

```
Gly Arg Lys Arg Lys Lys Arg Thr
1               5
```

<210> SEQ ID NO 20
<211> LENGTH: 16
<212> TYPE: PRT
<213> ORGANISM: Drosophila sp.

<400> SEQUENCE: 20

```
Arg Gln Ile Lys Ile Trp Phe Gln Asn Arg Arg Met Lys Trp Lys Lys
1               5                   10                  15
```

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Arg Gln Leu Lys Leu Trp Phe Gln Asn Arg Arg Met Lys Trp Lys Lys
1               5                   10                  15
```

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Arg Glu Ile Lys Ile Trp Phe Gln Asn Arg Arg Met Lys Trp Lys Lys
1               5                   10                  15
```

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 23

Lys Glu Thr Trp Trp Glu Thr Trp Trp Thr Glu Trp Ser Gln Pro Lys
1               5                   10                  15

Lys Arg Lys Val
            20

<210> SEQ ID NO 24
<211> LENGTH: 16
<212> TYPE: PRT
<213> ORGANISM: Rattus sp.

<400> SEQUENCE: 24

Pro Val Ile Arg Val Trp Phe Gln Asn Lys Arg Cys Lys Asp Lys Lys
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(12)
<223> OTHER INFORMATION: This region may encompass 1-6 residues

<400> SEQUENCE: 25

Arg Arg Arg Arg Arg Arg Arg Arg Arg Arg Arg Arg
1               5                   10

<210> SEQ ID NO 26
<211> LENGTH: 16
<212> TYPE: PRT
<213> ORGANISM: Mus sp.

<400> SEQUENCE: 26

Leu Leu Ile Ile Leu Arg Arg Arg Ile Arg Lys Gln Ala His Ala His
1               5                   10                  15

<210> SEQ ID NO 27
<211> LENGTH: 16
<212> TYPE: PRT
<213> ORGANISM: Drosophila sp.

<400> SEQUENCE: 27

Arg Arg Leu Arg Arg Leu Leu Arg Arg Leu Leu Arg Arg Leu Arg Arg
1               5                   10                  15

<210> SEQ ID NO 28
<211> LENGTH: 12
<212> TYPE: PRT
<213> ORGANISM: Rabies virus

<400> SEQUENCE: 28

Arg Val Gly Arg Arg Arg Arg Arg Arg Arg Arg Arg
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 29

Arg Arg Trp Trp Arg Arg Trp Arg Arg
1               5

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 31
<211> LENGTH: 7
<212> TYPE: PRT
<213> ORGANISM: Simian virus 40

<400> SEQUENCE: 31

Pro Lys Lys Lys Arg Lys Val
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Gly Gly Arg Leu Ser Tyr Ser Arg Arg Phe Ser Thr Ser Thr Gly
1               5                   10                  15

Arg

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Arg Leu Ser Tyr Ser Arg Arg Arg Phe
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Gly Gly Arg Leu Ala Tyr Leu Arg Arg Arg Trp Ala Val Leu Gly
1               5                   10                  15

Arg
```

<210> SEQ ID NO 35
<211> LENGTH: 11
<212> TYPE: PRT
<213> ORGANISM: Human immunodeficiency virus

<400> SEQUENCE: 35

Tyr Gly Arg Lys Lys Arg Arg Gln Arg Arg Arg
1               5                   10

<210> SEQ ID NO 36
<211> LENGTH: 10
<212> TYPE: PRT
<213> ORGANISM: Human immunodeficiency virus

<400> SEQUENCE: 36

Tyr Gly Arg Lys Lys Arg Arg Gln Arg Arg
1               5                   10

<210> SEQ ID NO 37
<211> LENGTH: 9
<212> TYPE: PRT
<213> ORGANISM: Human immunodeficiency virus

<400> SEQUENCE: 37

Gly Arg Lys Lys Arg Arg Gln Arg Arg
1               5

<210> SEQ ID NO 38
<211> LENGTH: 13
<212> TYPE: PRT
<213> ORGANISM: Human immunodeficiency virus

<400> SEQUENCE: 38

Gly Arg Lys Lys Arg Arg Gln Arg Arg Arg Pro Pro Gln
1               5                   10

<210> SEQ ID NO 39
<211> LENGTH: 11
<212> TYPE: PRT
<213> ORGANISM: Homo sapiens

<400> SEQUENCE: 39

Gly Lys Lys Lys Lys Arg Lys Arg Glu Lys Leu
1               5                   10

<210> SEQ ID NO 40
<211> LENGTH: 8
<212> TYPE: PRT
<213> ORGANISM: Unknown
<220> FEATURE:
<223> OTHER INFORMATION: Description of Unknown:
      TFIIE-beta sequence

<400> SEQUENCE: 40

Ser Lys Lys Lys Lys Thr Lys Val
1               5

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Leu Ile Tyr Leu Arg Leu Leu Arg Gly Gln Phe
1               5                   10

<210> SEQ ID NO 44
<211> LENGTH: 34
<212> TYPE: PRT
<213> ORGANISM: Herpes simplex virus

<400> SEQUENCE: 44

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Any amino acid

<400> SEQUENCE: 45

Leu Xaa Xaa Xaa Xaa Xaa Xaa
1               5
```